United States Patent
Mandai et al.

[11] Patent Number: 6,136,990
[45] Date of Patent: Oct. 24, 2000

[54] TAXOID COMPOUND AND METHOD FOR PRODUCING THE SAME

[75] Inventors: Tadakatsu Mandai, 1174-371, Tsurajima, Tsurajima-cho, Kurashiki-shi, Okayama-ken; Hiroshi Okumoto, Okayama-ken; Katsuyoshi Nakanishi, Yokohama; Koji Hara, Yokohama; Katsuhiko Mikuni, Yokohama; Kozo Hara, Yokohama, all of Japan

[73] Assignees: Bio Research Corporation of Yokohama; Ensuiko Sugar Refining Co., Ltd., both of Yokohama; Tadakatsu Mandai, Kurashiki, all of Japan

[21] Appl. No.: 09/504,788

[22] Filed: Feb. 15, 2000

[30] Foreign Application Priority Data

Sep. 17, 1999 [JP] Japan .................. 11-263974

[51] Int. Cl.⁷ .................. C07D 305/14; C07D 409/00; C07D 405/00
[52] U.S. Cl. .................. 549/510; 549/60; 546/281.7
[58] Field of Search .................. 549/510, 60, 511; 546/281.7

[56] References Cited

U.S. PATENT DOCUMENTS

| | | | |
|---|---|---|---|
| 6,040,466 | 3/2000 | Bouchard et al. | 549/510 |
| 6,043,382 | 3/2000 | Nicolaou et al. | 549/510 |
| 6,051,724 | 4/2000 | Holton et al. | 549/510 |
| 6,066,747 | 3/2000 | Holton et al. | 549/510 |
| 6,066,748 | 5/2000 | Han et al. | 549/510 |
| 6,066,749 | 5/2000 | Sisti et al. | 549/510 |

*Primary Examiner*—Deborah C. Lambkin
*Attorney, Agent, or Firm*—Oblon, Spivak, McClelland, Maier & Neustadt, P.C.

[57] ABSTRACT

A taxoid compound represented by general formula (I)

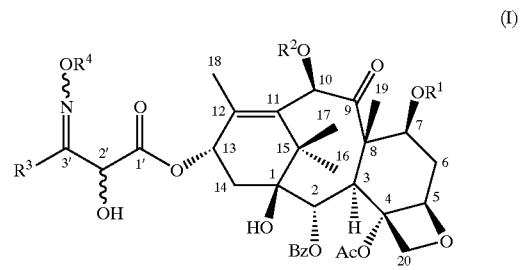

where the symbols $R^1$, $R^2$, $R^3$, $R^4$, Bz, and Ac have specified meanings. Also, a method for producing the taxoid derivative from a baccatin derivative having a β-ketoester group at the 13-position by transesterification and a method for producing taxoid compound such as paclitaxel from the taxoid derivative under mild condition are disclosed.

3 Claims, No Drawings

TAXOID COMPOUND AND METHOD FOR PRODUCING THE SAME

FIELD OF THE INVENTION

The present invention relates to a taxoid compound and a method for producing the same.

BACKGROUND OF THE INVENTION

Paclitaxel (trade name: Taxol) is a kind of anticancer agent that can be obtained from *Taxus Brevifolia* (yew tree), which is known to be effective particularly against breast cancer and lung cancer. However, the amount of paclitaxel that can be obtained from *Taxus Brevifolia* is very small, and there arises a problem in that the destruction of forests occurs, since the bark of trees is stripped to collect.

On the other hand, 10-deacetylbaccatin III that can be collected from leaves of yew trees are capable of being recollected, and are useful as a precursor for paclitaxel or its derivative, docetaxel (trade name: Taxotere), etc.

The synthetic method for the above substances are known as a semi-synthetic method, and there have been proposed (a) a method through β-lactam (European Patent No. 0400971), (b) a method using an oxazoline compound (International Patent Kokai No. Hei 7-504444), (c) a method using thioester compound (International Patent Kokai No. Hei 10-505360), (d) a method using cinnamic acid (Tetrahedron, Vol. 42, p.4451 (1986)), etc.

However, the above methods thus far developed involve subjects such as reaction under the condition of extremely low temperatures, generation of diastereomers, use of asymmetry controlling agents, and reaction under strongly alkaline conditions, which cause problems upon the industrialization thereof.

SUMMARY OF THE INVENTION

In view of the above-mentioned circumstances, the inventors of the present invention have made extensive investigations on a method for producing a taxoid compound, such as paclitaxel, suitable for industrial application, and have completed the present invention.

Accordingly, an object of the present invention is to provide a method for producing a taxoid derivative under mild conditions from a compound, as a starting material, having introduced a β-ketoester at the 13-position of baccatin by transesterification. Further, another object of the present invention is to provide a method for producing a taxoid compound such as paclitaxel using said taxoid derivative as a starting material.

According to a first aspect of the present invention, there is provided a taxoid derivative represented by general formula (I);

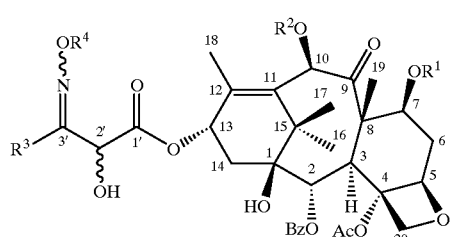

(I)

(where $R^1$ and $R^2$ simultaneously or independently represent a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^4$ represents any one of a benzyl group, a methyl group, or an ethyl group, Bz represents a benzoyl group, and Ac represents an acetyl group).

Further, according to a second aspect of the present invention, there is provided a method for producing a taxoid derivative, characterized in that the taxoid derivative as set forth in the first aspect of the present invention, represented by general formula (I) is obtained using as a starting material a baccatin compound represented by general formula (a);

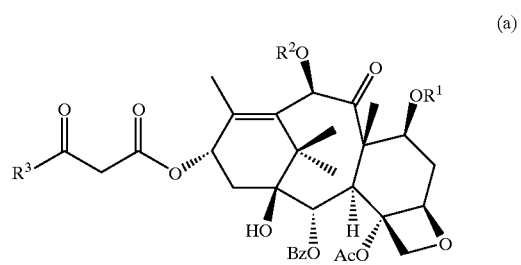

(a)

(where $R^1$ and $R^2$ simultaneously or independently represent a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, Bz represents a benzoyl group, and Ac represents an acetyl group), through intermediate compounds represented by general formulae (b), (c), and (d) in order;

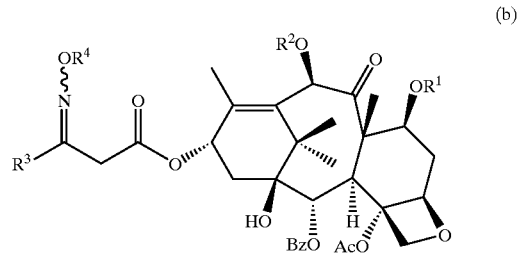

(b)

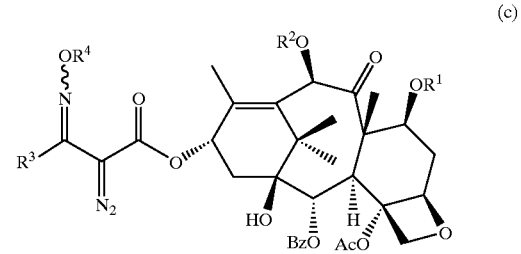

(c)

-continued (d)

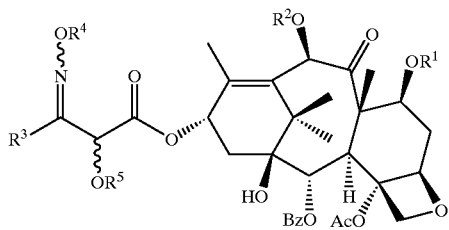

(IV)

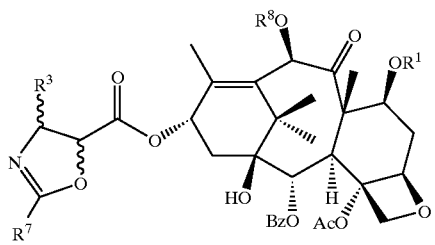

(in the above-mentioned formulae (b), (c), and (d), $R^1$ and $R^2$ simultaneously or independently represent a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^4$ represents any one of a benzyl group, a methyl group, or an ethyl group, $R^5$ represents an acyl group, Bz represents a benzoyl group, and Ac represents an acetyl group).

Still further, according to a third aspect of the present invention, there is provided a method for producing a taxoid compound, characterized in that the taxoid compound such as paclitaxel represented by general formula (V);

(V)

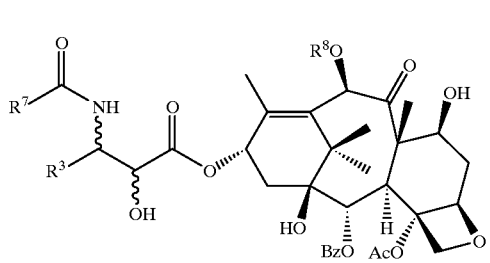

is obtained using as a starting material the taxoid derivative as set forth in the first aspect of the present invention through intermediate compounds represented by general formula (II), (III), and (IV) in order;

(II)

(III)

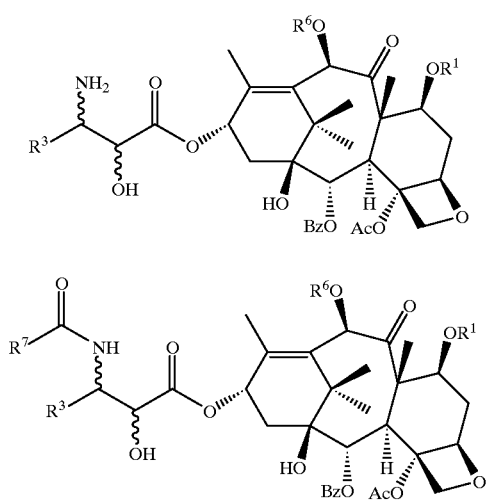

(in the above-mentioned formulae (II), (III), (IV), and (V), $R^1$ represents a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^6$ represents a hydrogen atom or a protective group for a hydroxyl group, $R^7$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^8$ represents a hydrogen atom or an acyl group, Bz represents a benzoyl group, and Ac represents an acetyl group).

DETAILED DESCRIPTION OF THE INVENTION

Hereinafter, the present invention will be described in detail.

The baccatin derivative used in the present invention can be obtained by reaction between 10-deacetylbaccatin III, represented by the formula (A) below, having introduced protective groups to the hydroxyl groups at the 7- and 10-positions, and a β-ketoester. This reaction is described in Japanese Patent Application No. Hei 11-218730 and No. Hei. 11-37055, and the baccatin derivative used in the present invention is represented by general formula (a) below.

(A)

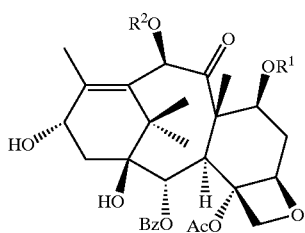

(a)

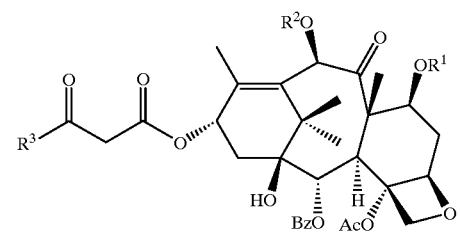

In the above general formulae (A) and (a), $R^1$ and $R^2$ simultaneously or independently represent a protective group for a hydroxyl group and include, for example, those protective groups described in "New Course of Experimental Chemistry, Vol. 14, Organic Synthesis V, Chapter 11–1, Ed. by Japan Chemical Association." Specifically, examples of such protective groups include a triethylsilyl group, a benzyloxycarbonyl group, an acetyl group, an allyloxycarbonyl group, etc.

$R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, Bz represents a benzoyl group, and Ac represents an acetyl group.

The baccatin used in the present invention may be 10-deacetylbaccatin III extracted from leaves of yew trees or its analogs, or compounds that can be obtained from low molecular compounds by synthesis. Particularly, 10-deacetylbaccatin III is suitable for effectively practicing the present invention.

The taxoid derivative is represented by general formula (I)

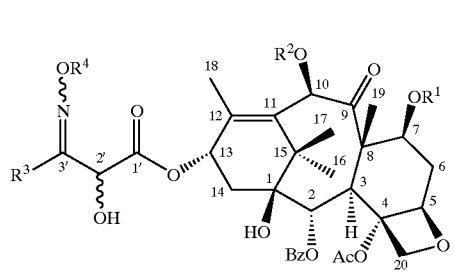

In the above formula, $R^1$, $R^2$, and $R^3$ represent the functional groups described above, $R^4$ represents any one of a benzyl group, a methyl group or an ethyl group, Bz represents a benzoyl group, and Ac represents an acetyl group.

The taxoid derivative represented by the general formula (I) can be produced from the baccatin derivative as a starting material represented by the general formula (a) by the following reaction scheme.

Reaction Scheme 1

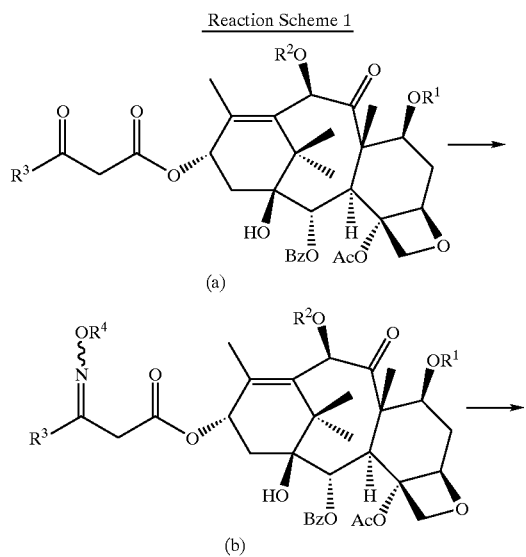

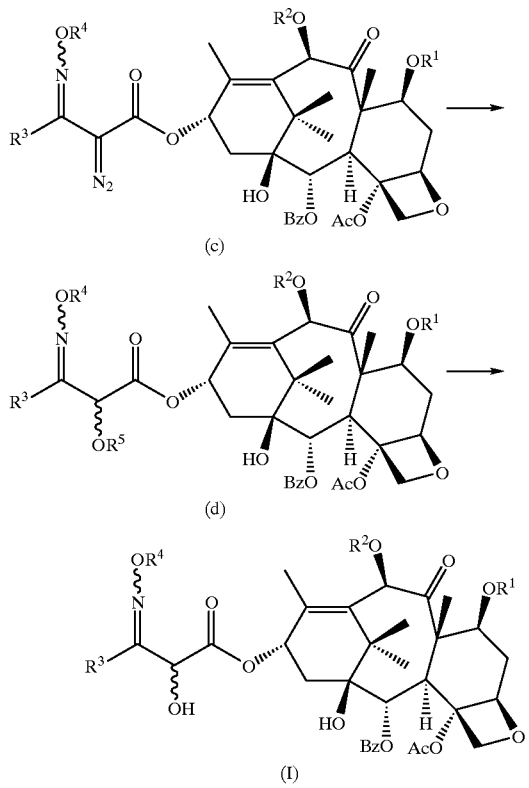

In the above formulae, $R^1$, $R^2_1$ and $R^3$ represent the functional groups described above, $R^4$ represents any one of a benzyl group, a methyl group or an ethyl group, $R^5$ represents an acyl group, Bz represents a benzoyl group, and Ac represents an acetyl group.

The reaction from compound (a) to compound (b) can be carried out in the presence of O-substituted hydroxylamine hydrochloride and an amine based solvent such as pyridine. Specific examples of the O-substituted hydroxylamine hydrochloride include O-benzylhydroxylamine hydrochloride, O-methylhydroxylamine hydrochloride, O-ethylhydroxylamine hydrochloride, etc.

The reaction from compound (b) to compound (c) can be carried out in the presence of an azide compound and an amine based solvent such as triethylamine, 1,8-diazabicyclo [5,4,0]-7-undecene (DBU). Here, tosyl azide is particularly suitable as the azide compound.

The reaction from compound (c) to compound (d) can be carried out in the presence of a metal complex and an acid based on acetic acid. As the metal complex, there may be used copper complexes, palladium complexes, etc. Copper acetylacetonate is used particularly preferably. The acid based on acetic acid specifically includes acetic acid, trichloroacetic acid, etc.

The reaction from compound (d) to compound (I) can be carried out in the presence of a tin compound and an alcohol. The tin compound specifically includes 1-chloro-3-hydroxytetrabutyldistanoxane. The alcohol specifically includes methanol, ethanol, etc.

To produce paclitaxel from the taxoid derivative represented by the general formula (I) as a starting material, the reaction may be carried out according to the following reaction scheme.

Reaction Scheme 2

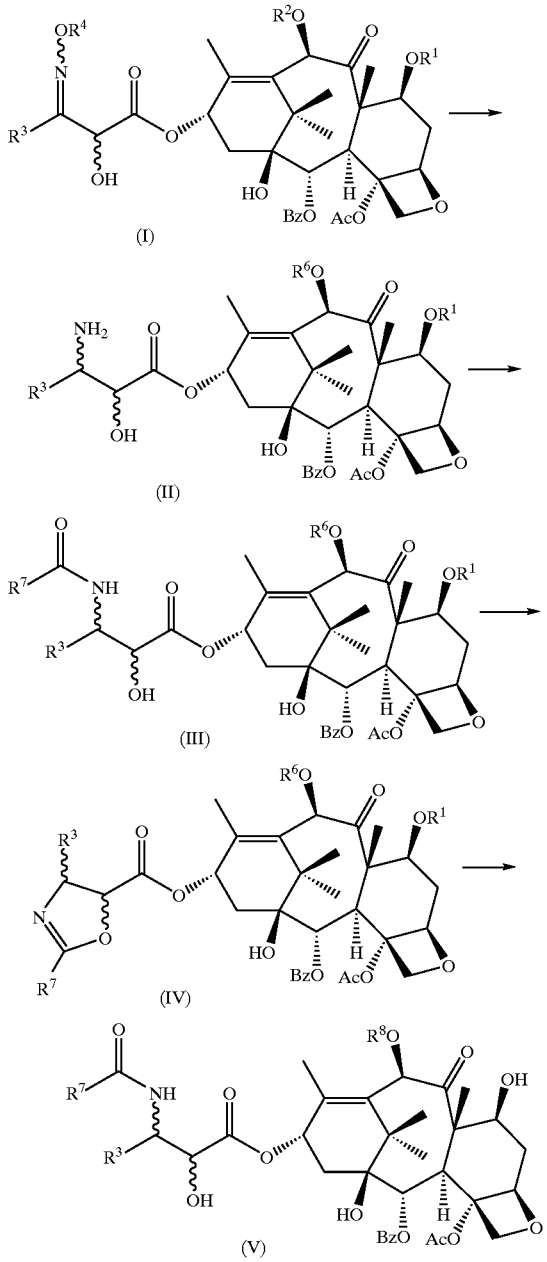

In the above formulae, $R^6$ represents a hydrogen atom, an acetyl group or the like, $R^7$ represents a phenyl group, a p-methoxyphenyl group, a monofluorophenyl group, a trifluoromethylphenyl group, a cyclohexyl group, or the like, $R^8$ represents a hydrogen atom or an acyl group such as an acetyl group or the like. Bz represents a benzoyl group, and Ac represents an acetyl group.

The reaction from compound (I) to (II) can be carried out in the presence of a palladium catalyst and a hydrogen donating compound (or hydrogen gas). As the palladium catalyst may be used palladium-carbon or palladium black. As a preferred hydrogen donating compound is used ammonium formate.

The reaction from compound (II) to compound (III) can be carried out in the presence of an acid chloride, ethyl acetate, and aqueous saturated sodium hydrogencarbonate. Specific examples of the acid chloride include benzoyl chloride, p-methoxybenzoyl chloride, p-trifluoromethylbenzoyl chloride, etc.

The reaction from compound (III) to compound (IV) can be carried out in the presence of an azo compound and a phosphorus compound. Preferably, the azo compound may be diethyl azodicarboxylate and the phosphorus compound may be triphenylphosphine.

The reaction from compound (IV) to compound (V) can be carried out by known methods. That is, a method described in Tetrahedron Letter, Vol. 35, p.4483 (1994), a method described in International Patent Kokai No. Hei 7-504444, a method described in International Patent Kokai No. Hei 10-505360, etc correspond thereto. Specifically, the reaction can be carried out in an acid solvent. As the acid solvent, an aqueous hydrochloric acid solution, acetic acid, etc may be used.

Hereinafter, the present invention will be specifically described with taking the case as a typical example, where a baccatin derivative is used in which the hydroxyl group at the 7-position is protected with a triethylsilyl group, the hydroxyl group at the 10-position is protected with a benzyloxycarbonyl group and the hydroxyl group at the 13-position is bonded through an ester bond introduced by transesterification with ethyl benzoylacetate.

Among the compounds represented by the general formula (I), the compound in which $R^3$ is a phenyl group and $R^4$ is a benzyl group, or among the compound (d), the compound in which $R^5$ is an acetyl group, can be produced by the following reaction scheme 3.

Reaction Scheme 3

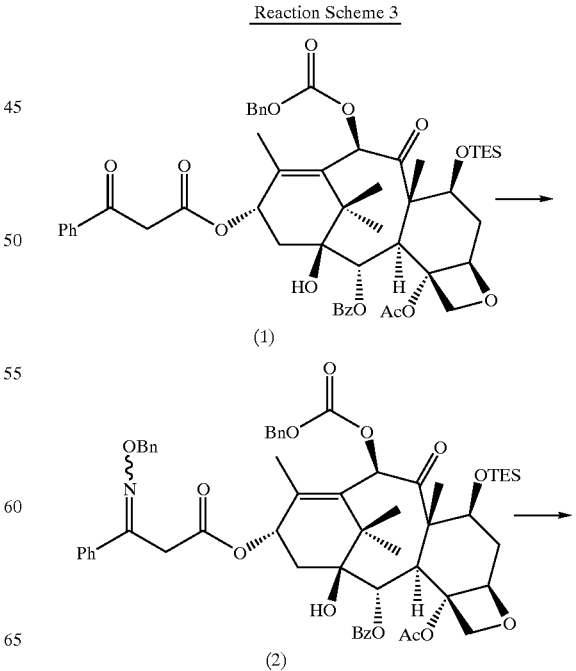

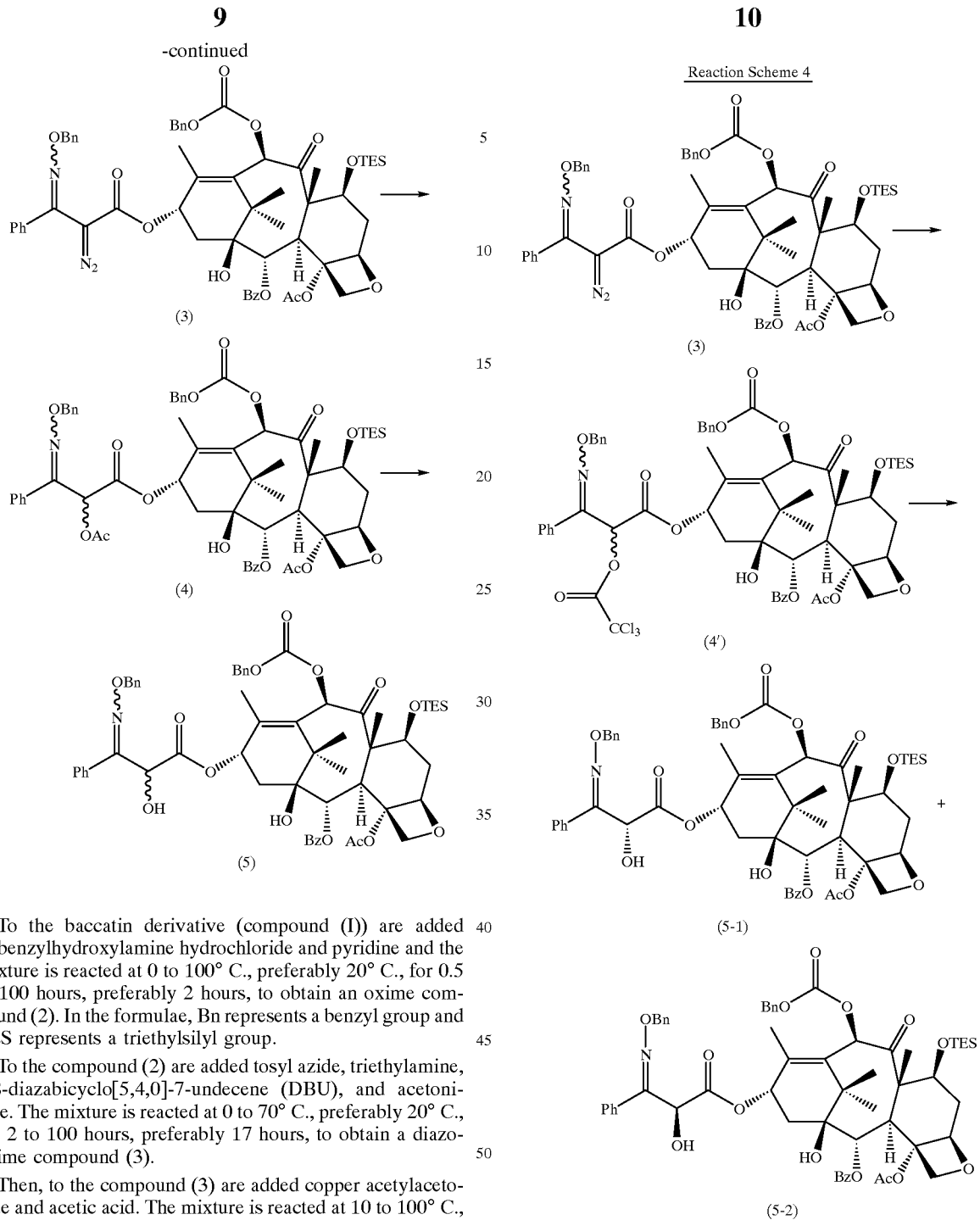

To the baccatin derivative (compound (I)) are added O-benzylhydroxylamine hydrochloride and pyridine and the mixture is reacted at 0 to 100° C., preferably 20° C., for 0.5 to 100 hours, preferably 2 hours, to obtain an oxime compound (2). In the formulae, Bn represents a benzyl group and TES represents a triethylsilyl group.

To the compound (2) are added tosyl azide, triethylamine, 1,8-diazabicyclo[5,4,0]-7-undecene (DBU), and acetonitrile. The mixture is reacted at 0 to 70° C., preferably 20° C., for 2 to 100 hours, preferably 17 hours, to obtain a diazooxime compound (3).

Then, to the compound (3) are added copper acetylacetonate and acetic acid. The mixture is reacted at 10 to 100° C., preferably 60° C., for 2 to 150 hours, preferably 84 hours, to obtain an acetoxyoxime compound (4).

To the compound (4) are added a tin compound and an ethanol. The mixture is reacted at 10 to 120° C., preferably 70° C., for 2 to 100 hours, preferably 37.5 hours, to obtain an oxime alcohol compound (5). This compound corresponds to the compound represented by the general formula (I) in which $R^3$ is a phenyl group and $R^4$ is a benzyl group. Note that the compound obtained by this method has EZ isomers on the oxime at the 3'-position and stereoisomers at the 2'-position and thus is a mixture of four isomers.

The production of compound (5) from compound (3) can be carried out by another reaction (reaction scheme 4) as follows.

To compound (3) are added copper acetylanetonate, trichloroacetic acid, and 1,3,5-trimethylbenzene (mesitylene). The mixture is reacted at −30° C. to 20° C., preferably 0° C., for 1.5 to 24 hours, preferably 3 hours, to obtain trichloroacetoxyoxime compound (4').

To the compound (4') are added a tin compound and ethanol. The mixture is reacted at 10 to 120° C., preferably 70° C., for 2 to 100 hours, preferably 37.5 hours, to obtain an oxime alcohol compounds (5-1) and (5-2). In this method, only stereoisomers of the hydroxyl group at the 2'-position are produced, which can be readily separated by silica gel column chromatography, etc. The separation eliminates the necessity of separation operation of stereoisomers afterwards.

Among the compounds represented by the general formula (IV), the compound in which $R^6$ is a hydrogen atom and $R^7$ is a phenyl group can be produced according to reaction scheme 5 as follows.

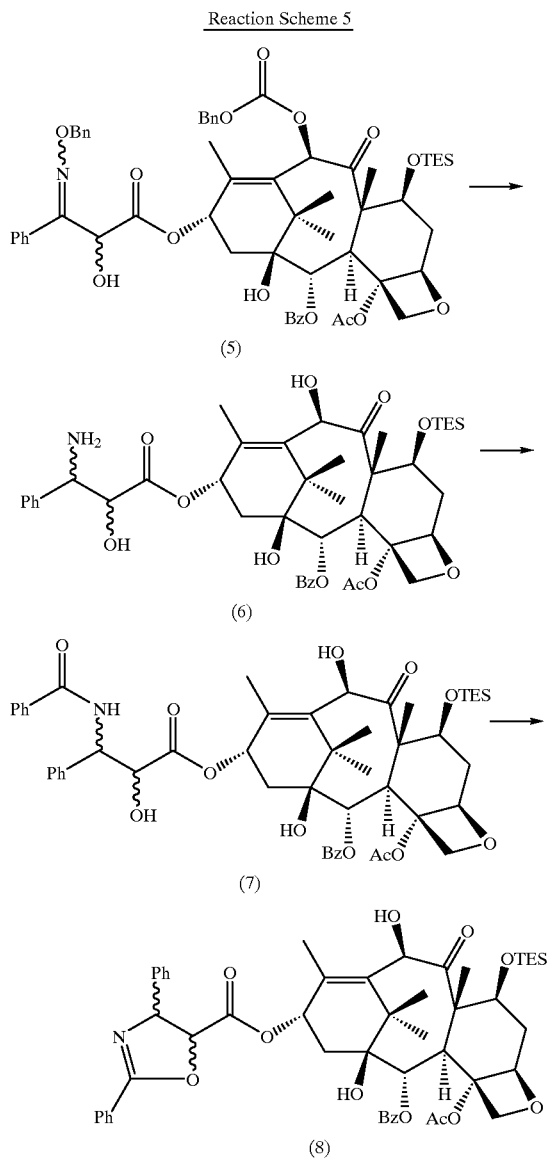

Reaction Scheme 5

To compound (5) are added 10% palladium-carbon, ammonium formate, and ethanol. The mixture is reacted at 0 to 70° C., preferably 20° C., for 2 to 150 hours, preferably 95 hours, to obtain an amino-alcohol compound (6).

Subsequently, to the compound (6) are added ethyl acetate, aqueous saturated sodium hydrogencarbonate, and benzoyl chloride. The mixture is reacted at 0 to 70° C., preferably 20° C., for 0.5 to 50 hours, preferably 1.5 hours, to obtain a benzoylamino-alcohol compound (7).

To the compound (7) are added diethyl azodicarboxylate, triphenylphosphine, and dichloromethane. The mixture is reacted at −15° C. to 50° C., preferably 0° C., for 0.5 to 100 hours, preferably 1.5 hours, to obtain an oxazoline compound (8). This compound corresponds to the compound represented by the general formula (IV) in which $R^6$ is a hydrogen atom and $R^7$ is a phenyl group.

In Reaction Scheme 5 above, diastereomers occur at the 2'- and 3'-positions of the side chain part of the compound (6). The diastereomers are two kinds of compounds of anti-type having different orientations of 2'- and 3'-positions (2'S, 3'S or 2'R, 3'R). The target compound, paclitaxel, has a stereospecific configuration (2'S, 3'R). The compound having a desired stereospecific configuration can be obtained by forming an oxazoline ring in the reaction from the compound (7) to the compound (8) to cause inversion of the stereospecific configuration at the 2'-position.

To obtain only the compound having a desired stereospecific configuration can be readily achieved by separation of the compound (7) or (8) using a column based on silica gel.

Separation of the isomers of the compound (8) using a column based on silica gel can be carried out by the following reaction scheme 6.

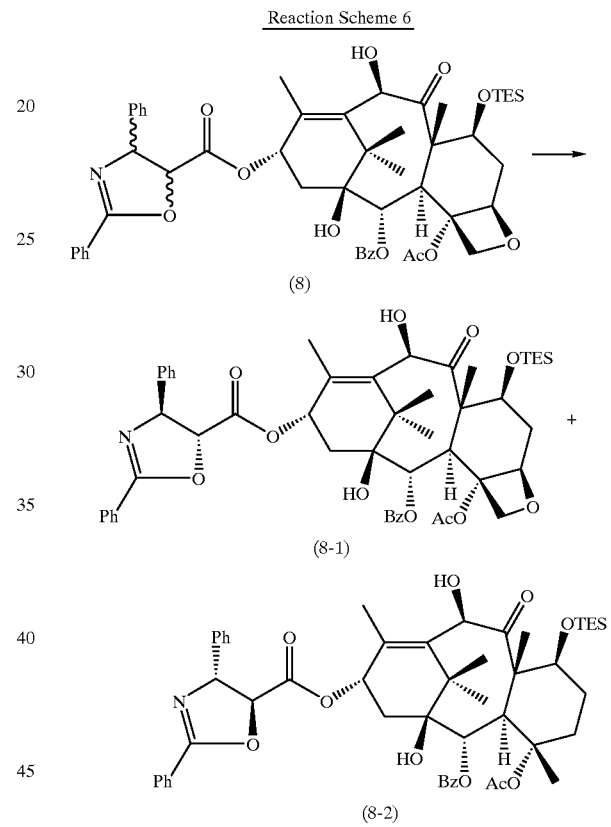

Reaction Scheme 6

After dissolving the compound (8) in methanol, the solution is applied to an ODS column, thereby conducting elution with a methanol/water base solvent to obtain respective isomers (8-1) and (8-2). What is required in the present invention is the compound (8-1) of which the oxazoline ring has a stereospecific configuration (4'S, 5'R) and in which the opening of the oxazoline ring results in the stereospecific configuration of the compound of (2'S, 3'R). The compound (8-2) of which the oxazoline ring has a stereospecific configuration (4'R, 5'S) and in which the opening of the oxazoline ring gives rise to an undesired stereospecific configuration of the compound of (2'R, 3'S) can be reused as a baccatin derivative by removing the functional group at the 13-position by alkali hydrolysis with an aqueous sodium hydroxide solution of about 2 N.

The reaction for obtaining paclitaxel from the compound (8-1) as a starting material can be carried out according to the following reaction scheme 7.

Reaction Scheme 7

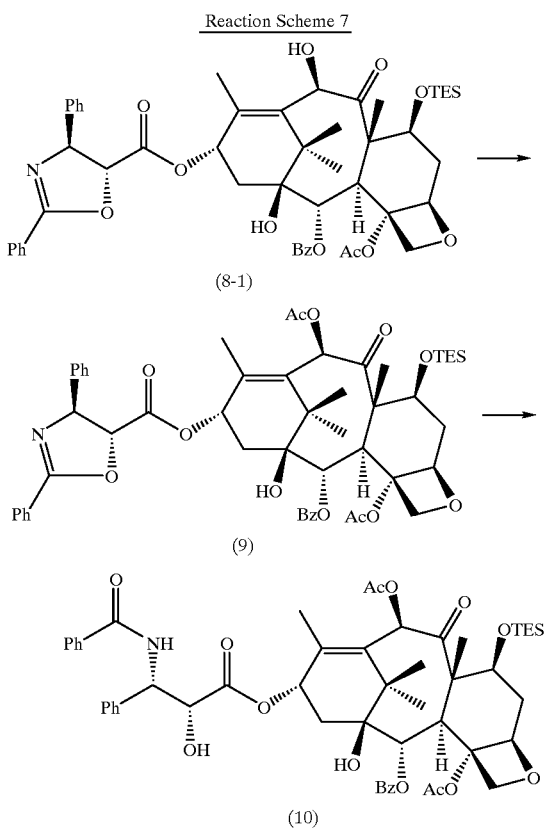

(8-1)

(9)

(10)

To the compound (8-1) are added acetic anhydride or acetyl chloride, pyridine, and optionally 4-dimethylaminopyridine. The mixture is reacted at 0 to 150° C., preferably 20° C., for 2 to 100 hours, preferably 40 hours, to obtain a compound (9) with its 10-position being acetylated.

To the compound (9) is added aqueous hydrochloric acid solution and methanol. The mixture is reacted at 0 to 100° C., preferably 60 to 80° C., for 1 to 10 hours, preferably 2.5 hours, added saturated sodium hydrogencarbonate solution, and further reacted at 0 to 60° C., preferably 20° C., for 10 to 50 hours, preferably 19 hours to obtain a compound (10). The compound (10) is paclitaxel.

The Reaction Schemes 3 to 7 above relate to the methods for producing paclitaxel. However, they can produce other taxoid compounds. For example, in the case where $R^3$ in the baccatin derivative (compound (I)) is not a phenyl group but is a p-methoxyphenyl group, a 2-furyl group, or a cyclopropyl group, taxoid derivatives in which the corresponding phenyl group at the 3'-position of paclitaxel compound is substituted by a p-methoxyphenyl group, a 2-furyl group, or a cyclopropyl group are obtained. In the case where the reagent to be reacted with the compound (6) in the Reaction Scheme 5 above is not benzoyl chloride but is a p-methoxybenzoyl chloride or p-trifluoromethylbenzoyl chloride, the taxoid compounds in which the corresponding benzoyl group on the amino group at the 3'-position of paclitaxel compound is replaced by p-methoxybenzoyl group or p-trifluoromethylbenzoyl group are obtained.

According to the present invention, there are provided novel taxoid derivatives and a method for producing the taxoid derivative from, as a starting material, a baccatin derivative having a β-ketoester group at the 13-position by transesterification under mild conditions. Also, there is provided a method for producing a taxoid compound such as paclitaxel from the compound of the present invention as a starting material.

EXAMPLES

Hereinafter, the present invention will be described in detail by examples. However, the present invention should not be construed as being limited thereto.

Production Example 1
(Production Method for Starting Material)

1.586 g of a compound (7-triethylsilyl-10-benzyloxycarbonyl-10-deacetylbaccatin III, $C_{43}H_{56}O_{12}Si$, molecular weight: 792.99) obtained from 10-deacetylbaccatin III according to the conventional method by protecting the hydroxyl group at the 7-position with a triethylsilyl group and the hydroxyl group at the 10-position with a benzyloxycarbonyl group, 6.9 ml of ethyl benzoylacetate, and 11 mg of 1-chloro-3-hydroxytetrabutyldistanoxane were reacted at 90° C. for 3 hours under reduced pressure (0.5 to 1 mmHg) to obtain an ester compound (7-triethylsilyl-10-benzyloxycarbonyl-10-deacetyl-13-(3-phenyl-3-keto-propanoyl)-baccatin III, compound (1), $C_{52}H_{62}O_{14}Si$, molecular weight of 939.14).

This compound was dissolved in chloroform-d and analyzed by $^1$H-NMR. Assignment of respective peaks was made to determine its chemical structure and thus it was confirmed to have a structure indicated as compound (1) in Reaction Scheme 3.

$^1$H-NMR (500 MHz, CDCl$_3$) of the ester compound (compound (1)).

σ(ppm).

0.52–0.63 (n, 6H), 0.86–0.95 (n, 9H), 1.17 (s, 0.70H*3), 1.19 (s, 0.30H*3),1.20 (s, 0.70H*3), 1.22 (s, 0.30H*3),1.69 (s, 0.70H*3),1.71 (s, 0.30H*3),1.85–1.95 (In 1H), 2.01 (d, J=0.9 Hz, 0.70H*3), 2.14 (d, J=0.9 Hz, 0.30H*3), 2.20–2.44 (n, 2H), 2.23 (s, 0.70H*3), 2.37 (s, 0.30H*3), 2.48–2.59 (m, 1H),3.79 (d, J=7.0 Hz, 0.70H), 3.84 (d, J=6.7 Hz, 0.30H), 4.09–4.20 (m, 1H+0.70H*2),4.26–4.33 (m, 1H), 4.45 (dd, J=6.7, 10.7 Hz, 0.70H), 4.50 (dd, J=6.7, 10.4 Hz, 0.30H), 4.92 (bd, J=7.9 Hz, 0.70l), 4.97 (bd, J=8.3H, 0.30H), 5.16–5.22 (ABq, J=12.2 Hz, 0.70H*2), 5.17, 5.24 (ABq, J=12.2 Hz, 0.30H*2), 5.63–5.72 (m, 1H), 5.75 (s, 0.30H), 6.19–6.30 (n, 1H), 6.27 (s, 0.70H), 6.32 (s, 0.30H), 7.30–7.68 (m, 11H), 7.78–7.85 (m, 0.30H*2), 7.95–8.03 (m, 0.70H*2), 8.03–8.12 (m, 2H), 12.51 (s, 0.30H).

Example 1
Production Method of Oxime Alcohol Compound—(1)

To 470 mg of the ester compound (1) obtained in Production Example 1 were added 160 mg of 0-benzylhydroxylamine hydrochloride and 2 ml of pyridine and the mixture was reacted at room temperature for 2.5 hours to obtain an oxime compound (compound (2), $C_{59}H_{69}NO_{14}Si$, molecular weight of 1,044.28).

To 519 mg of the compound (2) were added 2 ml of acetonitrile, 128 mg of tosyl azide, 0.09 ml of triethylamine, and 0.02 ml of 1,8-diazabicyclo [5.4.0]-7-undecene and the mixture was reacted at room temperature for 17 hours to obtain a diazo-oxime compound (compound (3)), $C_{59}H_{67}N_3O_{14}Si$, molecular weight of 1,070.28).

To 465 mg of the compound (3) were added 226 mg of copper acetylacetonate and 3 ml of acetic acid and the mixture was reacted at 70° C. for 84 hours to obtain an acetoxyoxime compound (compound (4), $C_{61}H_{71}NO_{16}Si$, molecular weight of 1,102.31).

Then, to 381 mg of the compound (4) were added 5 mg of 1-chloro-3-hydroxytetrabutyldistanoxane and 5 ml of ethanol and the mixture was reacted at 70° C. for 37.5 hours to obtain an oxime alcohol compound (compound (5), $C_{59}H_{69}NO_{15}Si$, molecular weight of 1,060.28). This compound was dissolved in chloroform-d and analyzed by $^1$H-NMR. Assignment of respective peaks was made to determine its chemical structure and thus it was confirmed to have a structure indicated as compound (5) in Reaction Scheme 3.

$^1$H-NMR (500 MHz, $CDCl_3$) of the oxime alcohol compound (compound (5)).

σ(ppm).

0.50–0.65(m, 6H, TES), 0.87–0.96(m, 9H, TES), 1.15(s), 1.19(s), 1.56(s), 1.68(s), 1.73(s), 1.98(s), 2.09(s), 2.19(s), 2.35(s), 1.61–2.60(m, 4), 3.49–3.80(m, 2H), 4.09–4.50(m, 3H), 4.80–5.00(m, 1H), 5.10–5.40(m, 5H), 5.59–5.70(m, 1H), 6.06–6.30(m, 2H), 7.1–7.7(m, 18H, Ar), 8.02–8.12(m, 2H, Ar).

Example 2
Production Method of Oxime Alcohol Compound—(2)

To obtain the oxime alcohol compound (compound (5)) from the diazo-oxime compound (compound (3)), another reaction could be carried out.

To 583 mg of the compound (3) were added 141 mg of copper acetylacetonate, 2.65 g of trichloroacetic acid, and 10 ml of 1,3,5-trimethylbenzene (mesitylene) and the mixture was reacted at 0° C. for 2.5 hours to obtain a trichloroacetoxyoxime compound (4'), $C_{61}H_{68}Cl_3NO_{16}Si$, molecular weight of 1,205.65).

To 7.819 g of the compound (4') were added 1.5 ml of 1-chloro-3-hydroxytetrabutyldistanoxane (1 mg/ml ethanol solution) and 4.5 ml of ethanol and the mixture was reacted at 50 to 75° C. for 18 hours. Thereafter, 1,3,5-trimethylbenzene (mesitylene) was removed under reduced pressure and the residue was purified using a silica gel column to obtain oxime alcohol compounds, i.e., 2'-α form, (compound (5-1), $C_{59}H_{69}NO_{15}Si$, molecular weight of 1,060.28) and 2'-β form, (compound (5-2), $C_{59}H_{69}NO_{15}Si$, molecular weight of 1,060.28).

The respective compounds were allowed to dissolve in chloroform-d and analyzed by $^1$H-NMR. Assignment of respective peaks was made to determine their chemical structure and thus they were confirmed to have structures indicated as compounds (5-1) and (5-2) in Reaction Scheme 4.

$^1$H-NMR (500 MHz, $CDCl_3$) of the oxime alcohol compound (compound (5-1)).

σ(ppm).

0.53–0.60(m, 6H, TES), 0.90(t, J=7.6 Hz, 9H, TES), 1.10(s,3H, 17-$CH_3$), 1.17(s, 3H, 16-$CH_3$), 1.61–2.06(m, 3H), 1.66(s,3H, 19-$CH_3$), 1.89(s, 3H, 18-$CH_3$), 1.98 (s, 3H, 4-Ac), 2.44–2.52(m, 1H, 6 α-H), 3.68(d, J=7.1 Hz, 1H, 3-H), 3.77(d, J=8.9 Hz, 1H, OH), 4.11(d, J=8.4 Hz, 1H, 20 β-H), 4.25(d, J=8.4 Hz, 1H, 20 α-H), 4.40(dd, J=6.7, 10.7 Hz, 1H, 7-H), 4.86(d, J=7.9 Hz, 1H, 5-H), 5.16–5.35(m, 5H, Bnx2, 2'-H), 5.60(d, J=7.1 Hz, 1H, 2-H), 5.93(t, J=7.6 Hz, 1H, 13-H), 6.21(s, 1H, 10-H), 7.20–7.70(m, 18H, Ar), 8.05(d, J=7.1 Hz, 2H, Ar).

$^1$H-NMR (500 MHz, $CDCl_3$) of the oxime alcohol compound (compound (5-2)).

σ(ppm).

0.51–0.65(m, 6H, TES), 0.92(t, J=7.6 Hz, 9H, TES), 1.19(s, 3H, 17-$CH_3$), 1.24(s, 3H, 16-$CH_3$), 1.68(s,3H, 19-$CH_3$), 1.73(s, 3H, 18-$CH_3$), 1.82–1.96(m, 1H, 6 β-H), 2.15–2.25(m, 1H, 14-H), 2.20 (s, 3H, Ac), 2.27–2.40 (m, 1H, 14-H), 2.48–2.59(m, 1H, 6 α-H), 3.54(d, J=7.9 Hz, 1H, OH), 3.74(d, J=7.2 Hz, 1H, 3-H), 4.14(d, J=8.4 Hz, 1H, 20 β-H), 4.28(d, J=8.4Hz, 1H, 20 α-H), 4.43(dd, J=6.7, 10.6 Hz, 1H, 7-H), 5.10–5.29(m, 5H, 5-H, Bnx2, 2'-H), 5.65(d, J=7.2 Hz, 1H, 2-H), 6.10(t, J=8.0 Hz, 1H, 13-H),6.21(s, 1H, 10-H), 7.30–7.65(m, 18H, Ar), 8.05(d, J=7.3 Hz, 2H, Ar).

Example 3
Production Method for Benzoylamino-alcohol Compound—(1)

To 345 mg of oxime alcohol compound (5) were added 5 ml of ethanol, 100 mg of 10% palladium-carbon, 416 mg of ammonium formate and the mixture was reacted at room temperature for 95 hours to obtain an amino-alcohol compound (compound (6), $C_{44}H_{59}NO_{12}Si$, molecular weight of 822.04).

To 281 mg of the compound (6) were added 2 ml of ethyl acetate, 2 ml of aqueous saturated sodium hydrogencarbonate, and 0.077 ml of benzoyl chloride and the mixture was reacted at room temperature for 1.5 hours to obtain a benzoylamino-alcohol compound (compound (7), $C_{51}H_{63}NO_{13}Si$, molecular weight of 926.14).

This compound was dissolved in chloroform-d and analyzed by $^1$H-NMR. Assignment of respective peaks was made to determine its chemical structure and thus it was confirmed to have a structure indicated as compound (7) in Reaction Scheme 5.

$^1$H-NMR (500 MHz, $CDCl_3$) of the benzoylamino-alcohol compound (compound (7)).

σ(ppm).

0.53–0.62(m, 6H, TES), 0.87–0.96(m, 9H, TES), 1.12(s), 1.14(s), 1.20(s), 1.21(s), 1.66(s), 1.67–2.58(m, 4H), 1.68(s), 2.02(s), 2.14(s), 3.28–3.41(m, 1H), 3.75–3.80(m, 1H), 4.13–4.35(m, 2H), 4.40–4.52(m, 1H), 4.70–4.89(m, 2H), 5.10 (s), 5.12(s), 5.60–5.85(m, 2H), 7.15–8.32(m, 15H, Ar).

Example 4
Production Method for Oxazoline Compound—(1)

To 218 mg of the benzoylamino-alcohol compound (7) were added 3 ml of dichloromethane, 94 mg of triphenylphosphine, and 0.057 ml of diethyl azodicarboxylate and the mixture was reacted at 0° C. for 1.5 hours to obtain an oxazoline compound (compound (8), $C_{51}H_{61}NO_{12}Si$, molecular weight of 908.13).

This compound was dissolved in chloroform-d and analyzed by $^1$H-NMR. Assignment of respective peaks was made to determine its chemical structure and thus it was confirmed to have a structure indicated as compound (8) in Reaction Scheme 5.

$^1$H-NMR (500 MHz, $CDCl_3$) of the oxazoline compound (compound (8)).

σ(ppm).

0.47–0.63(m, 6H, TES), 0.90–1.01(m, 9H, TES), 1.11(s, 3H, 17-$CH_3$),1.23(s, 3H, 16-$CH_3$), 1.68–2.06(m, 4H), 1.74 (s, 3H, 19-$CH_3$), 1.90(s, 18-$CH_3$), 1.95(s, 18-$CH_3$), 2.06 (s, 3H, Ac), 3.60–3.81(m, 3H), 3.89(d, J=7.2 Hz, 1H, 3-H), 4.41(dd, J=6.8, 10.7Hz, 1H, 7-H), 4.87–5.17(m, 3H), 5.55–5.67(m, 2H), 6.22(t, J=8.4 Hz, 13-H), 6.34(t, J=8.8 Hz, 13-H), 7.32–7.65(m, 11H, Ar), 8.02–8.27(m, 4H, Ar).

Example 5
Separation of Diastereomers—(1)

116 mg of the compound (8) obtained in Example 4 was subjected to separation of diastereomers using an ODS column. The separation conditions were as follows.

Column: Soken-pak φ100 mm×500 mm (Soken Kagaku)

Solvent: Methanol/water=90/10

Flow rate: 125 ml/minute

Detector: Ultraviolet detector (230 nm)

Under the above conditions, two fractions were obtained, which were each concentrated to obtain 49 mg of the compound (8-1) having a desired stereospecific configuration (4'S, 5'R) and 23 mg of the compound (8-2) having an undesired stereospecific configuration (4'R, 5'S). These respective compounds were dissolved in chloroform-d and analyzed by $^1$H-NMR. Assignment of respective peaks was made to determine their chemical structure and thus they were confirmed to have structures indicated as compound (8-1) and (8-2) in Reaction Scheme 6.

$^1$H-NMR (500 MHz, CDCl$_3$) of the compound having a stereospecific configuration (4'S, 5'R) (compound (8-1)).

σ(ppm).

0.47–0.62(m, 6H, TES), 0.93(t, J=8.25 Hz, 9H, TES), 1.11(s,3H, 17-CH$_3$), 1.23(s, 3H, 16-CH$_3$), 1.67(s, 1H, OH), 1.74(s,3H, 19-CH$_3$), 1.88–1.96(m, 1H, 6 β-H), 1.90(s, 3H, 18-CH$_3$), 2.06 (s, 3H, Ac), 2.24(dd, J=8.5, 15.3 Hz, 1H, 14-H), 2.37(dd, J=9.3, 15.3 Hz, 1H, 14-H), 2.49(ddd, J=6.5, 9.3, 14.3 Hz, 1H, 6 α-H), 3.89(d, J=7.2 Hz, 1H, 3-H), 4.16(d, J=8.5 Hz, 1H, 20 β-H), 4.25(d, J=1.8 Hz, 1H, 10-OH), 4.30(d, J=8.5 Hz, 1H, 20 α-H), 4.41(dd, J=6.5, 10.5 Hz, 1H, 7-H), 4.94(d, J=9.3 Hz, 1H, 5-H), 4.95(d, J=6.5 Hz, 1H, 2'-H), 5.10(d, J=1.8 Hz, 1H, 10-H), 5.61(d, J=6.5 Hz, 1H, 3'-H), 5.65(d, J=7.2 Hz, 1H, 2-H), 6.22(dd, J=8.5, 9.3 Hz, 1H, 13-H), 7.35–7.43(m, 5H, Ar), 7.46–7.52(m, 4H, Ar), 7.55–7.65(m, 2H, Ar), 8.07(d, J=7.3 Hz, 2H, Ar),8.23(d, J=7.3 Hz, 2H, Ar).

$^1$H-NMR (500 MHz, CDCl$_3$) of the compound having a stereospecific configuration (4'R, 5'S) (compound (8-2)).

σ(ppm).

0.50–0.63(m, 6H, TES), 0.96(t, J=8.25 Hz, 9H, TES), 1.12(s,3H, 17-CH$_3$), 1.24(s, 3H, 16 -CH$_3$), 1.65(s, 1H, OH), 1.74(s,3H, 19-CH$_3$), 1.88–2.06(m, 1H, 6 β-H), 1.95(s, 3H, 18-CH$_3$), 2.06 (s, 3H, Ac), 2.23(dd, J=8.5, 15.2 Hz, 1H, 14-H), 2.34(dd, J=9.2, 15.2 Hz, 1H, 14-H), 2.48(ddd, J=6.8, 9.7, 14.4 Hz, 1H, 6 α-H), 3.89(d, J=7.2 Hz, 1H, 3-H), 4.16(d, J=8.6 Hz, 1H, 20 β-H), 4.28(d, J=8.6 Hz, 1H, 20 α-H), 4.28(d, J=1.8 Hz, 1H, 10-OH), 4.42(dd, J=6.4, 10.7 Hz, 1H, 7-H), 4.90(d, J=9.7 Hz, 1H, 5-H), 4.97(d, J=6.2 Hz, 1H, 2'-H), 5.15(d, J=1.8 Hz, 1H, 10-H), 5.57(d, J=6.2 Hz, 1H, 3'-H), 5.65(d, J=7.2 Hz, 1H, 2-H), 6.34(dd, J=8.5, 9.2 Hz, 1H, 13-H), 7.35–7.52(m, 9H, Ar), 7.55–7.63(m, 2H, Ar), 8.06(dd, J=1.6, 7.0 Hz, 2H, Ar), 8.09(dd, J=1.6, 7.6 Hz, 2H, Ar).

Example 6

Production Method for Paclitaxel

To 83 mg of the oxazoline compound having the target stereospecific configuration (compound (8-1)) obtained in Example 5 were added 0.025 ml of acetic anhydride, 3 ml of pyridine, and 1 mg of 4-dimethylaminopyridine and the mixture was reacted at 0° C. to room temperature for 40 hours to obtain an oxazoline compound of which the 10-position was acetylated (compound (9), C$_{53}$H$_{63}$NO$_{13}$Si, molecular weight of 950.17).

To 85 mg of said compound (9) were added 4 ml of 0.1 N aqueous hydrochloric acid solution and 6 ml of methanol and the mixture was reacted at 60° C. for 1 hour and subsequently at 80° C. for 2 hours under reflux. After cooling the reaction mixture to room temperature, 2 ml of aqueous saturated sodium hydrogencarbonate was added thereto and the mixture was reacted at room temperature for 16 hours. After the treatment, the reaction mixture was purified through a silica gel column to obtain a compound (10). This compound was paclitaxel. The compound was dissolved in chloroform-d and analyzed by $^1$H-NMR. Assignment of respective peaks was made and thus it was confirmed that the compound was paclitaxel.

$^1$H-NMR (500 MHz, CDCl$_3$) of paclitaxel (compound (10)).

σ(ppm).

1.15(s, 3H, 17-CH$_3$),1.25(s, 3H, 16-CH$_3$),1.69(s, 3H, 19-CH$_3$),1.80(s, 3H, 18-CH$_3$),2.24(s, 3H, 4-Ac), 2.39(s, 3H, 10-Ac), 1.85–1.92(m, 1H, 6 β-H), 2.26–2.38(m, 2H, 14-H), 2.44–2.47(m, 1H, OH), 2.52–2.59(m, 1H, 6 α-H), 3.53(d, J=4.8Hz, 1H, OH), 3.80(d, J=6.7Hz, 1H, 3-H), 4.20(d, J=8.5Hz, 1H, 20 β-H), 4.31(d, J=8.5Hz, 1H, 20 α-H), 4.38–4.44(m, 1H, 7-H), 4.78–4.81(m, 1H, 2'-H), 4.95(dd, J=1.5, 9.5Hz, 1H, 5-H), 5.68(d, J=7.0Hz, 1H, 2-H), 5.79(dd, J=2.5, 9.0Hz, 1H, 3'-H), 6.24(t, J=9.3Hz, 1H, 13-H), 6.27(s, 1H, 10-H), 6.97(d, J=9.0Hz, 1H, 3'-NH), 7.34–7.77(m, 13H, Ar), 8.14(d, J=7.3Hz, 2H, Ar).

Example 7

Production Method for Oxime Alcohol Compound—(3)

In Example 1, the 10-position of the baccatin was protected with a benzyloxycarbonyl group. If the protective group was an acetyl group (i.e., if the compound was 7-triethylsilyl-13-(3-phenyl-3-keto-propanoyl)-baccatin III), paclitaxel could be prepared from the taxoid derivative similarly. To obtain an oxime alcohol compound, the reaction was run according to Reaction Scheme 8 below.

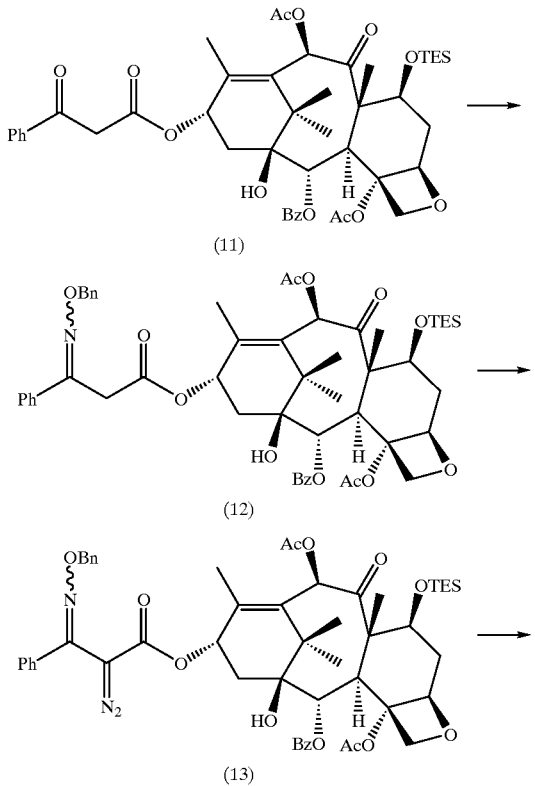

Reaction Scheme 8

-continued

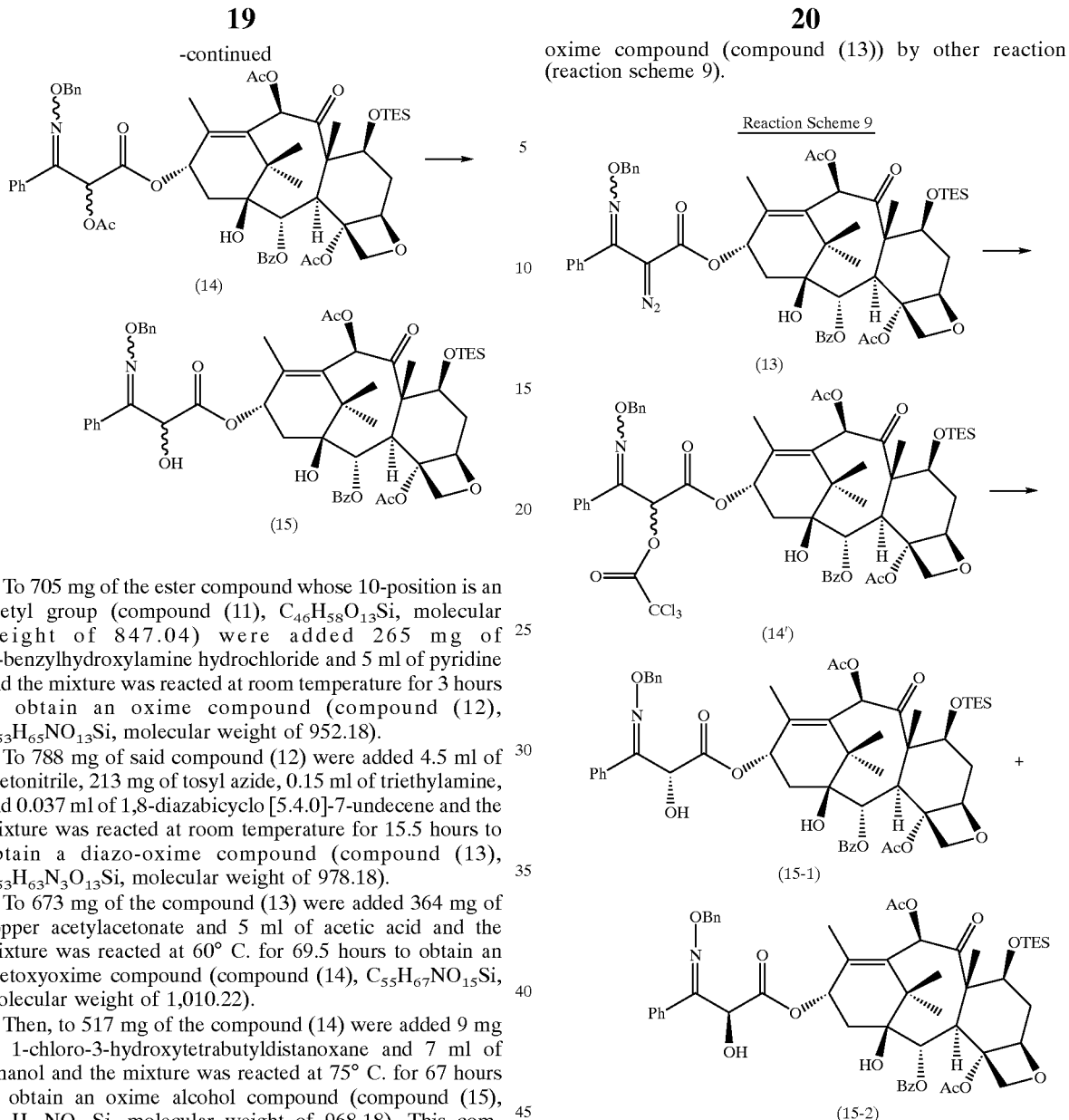

To 705 mg of the ester compound whose 10-position is an acetyl group (compound (11), $C_{46}H_{58}O_{13}Si$, molecular weight of 847.04) were added 265 mg of O-benzylhydroxylamine hydrochloride and 5 ml of pyridine and the mixture was reacted at room temperature for 3 hours to obtain an oxime compound (compound (12), $C_{53}H_{65}NO_{13}Si$, molecular weight of 952.18).

To 788 mg of said compound (12) were added 4.5 ml of acetonitrile, 213 mg of tosyl azide, 0.15 ml of triethylamine, and 0.037 ml of 1,8-diazabicyclo [5.4.0]-7-undecene and the mixture was reacted at room temperature for 15.5 hours to obtain a diazo-oxime compound (compound (13), $C_{53}H_{63}N_3O_{13}Si$, molecular weight of 978.18).

To 673 mg of the compound (13) were added 364 mg of copper acetylacetonate and 5 ml of acetic acid and the mixture was reacted at 60° C. for 69.5 hours to obtain an acetoxyoxime compound (compound (14), $C_{55}H_{67}NO_{15}Si$, molecular weight of 1,010.22).

Then, to 517 mg of the compound (14) were added 9 mg of 1-chloro-3-hydroxytetrabutyldistanoxane and 7 ml of ethanol and the mixture was reacted at 75° C. for 67 hours to obtain an oxime alcohol compound (compound (15), $C_{53}H_{65}NO_{14}Si$, molecular weight of 968.18). This compound was dissolved in chloroform-d and analyzed by $^1$H-NMR. Assignment of respective peaks was made to determine its chemical structure and thus it was confirmed to have a structure indicated as compound (15) in Reaction Scheme 8.

$^1$H-NMR (500 MHz, $CDCl_3$) of the oxime alcohol compound (compound (15)).

σ(ppm).

0.52–0.64(m, 6H, TES), 0.88–0.98(m, 9H, TES), 1.16(s), 1.21(s), 1.50–1.75(m, 1H), 1.67(s), 1.71(s), 1.83–2.38(m, 2H), 2.18(s), 2.20(s), 2.46–2.58(m, 1H), 3.42–3.58(m, 1H), 3.70–3.80(m, 1H), 4.09–4.48(m, 3H), 4.86–4.95(m, 1H), 5.10–5.38(m, 3H), 5.60–5.72(m, 1H), 6.07–6.19(m, 1H), 6.35–6.45(m, 1H), 7.18–7.68(m, 13H, Ar), 8.00–8.10(m, 2H, Ar).

Example 8
Production Method for Oxime Alcohol Compound—(4)

Similarly to the case where the 10-position of the compound was a benzyloxycarbonyl group, the hydroxyoxime compound (compound (15)) can be obtained from the diazo-oxime compound (compound (13)) by other reaction (reaction scheme 9).

Reaction Scheme 9

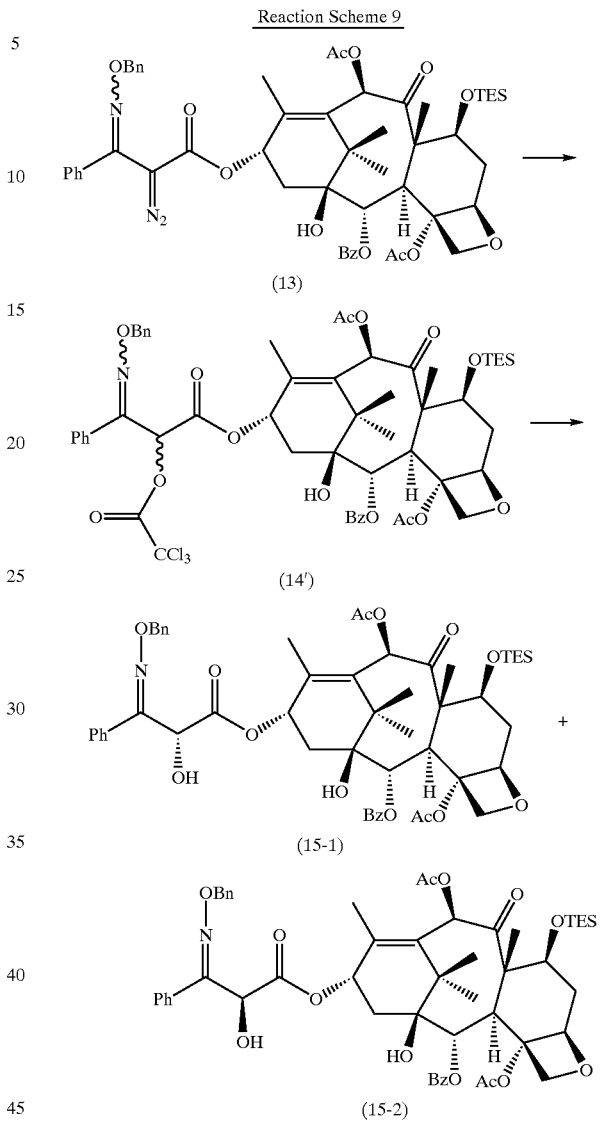

To 245 mg of the compound (13) were added 65 mg of copper acetylacetonate, 1.23 g of trichloroacetic acid, and 5 ml of 1,3,5-trimethylbenzene (mesitylene) and the mixture was reacted at 0° C. for 4.5 hours to obtain a trichloroacetoxyoxime compound (compound (14'), $C_{55}H_{64}Cl_3NO_{15}Si$, molecular weight of 1,113.55).

To 3.314 g of the compound (14') were added 1 ml of 1-chloro-3-hydroxytetrabutyldistanoxane (1 mg/ml ethanol solution) and 4 ml of ethanol and the mixture was reacted at 50 to 60° C. for 19 hours. Thereafter, 1,3,5-trimethylbenzene (mesitylene) was removed under reduced pressure and the residue was purified using a silica gel column to obtain oxime alcohol compounds, i.e., 2'-α form, (compound (15-1), $C_{53}H_{65}NO_{14}Si$, molecular weight of 968.18) and 2'-β form, (compound (15-2), $C_{53}H_{65}NO_{14}Si$, molecular weight of 968.18).

The respective compounds were dissolved in chloroform-d and analyzed by $^1$H-NMR. Assignment of respective peaks was made to determine their chemical structure and thus they were confirmed to have structures indicated as compounds (15-1) and (15-2) in Reaction Scheme 9.

$^1$H-NMR (500 MHz, CDCl$_3$) of the oxime alcohol compound (compound (15-1)).

σ(ppm).

0.50–0.65(m, 6H, TES), 0.92(t J=7.95 Hz, 9H, TES), 1.10(s,3H, 17-CH$_3$), 1.19(s, 3H, 16-CH$_3$),1.65(s,3H, 19-CH$_3$),1.75–1.90(m, 1H, 6 β-H), 1.89(s, 3H, 18-CH$_3$), 1.94–2.25(m, 2H, 14-H), 1.97(s, 3H, 4-Ac), 2.19(s, 3H, 10-Ac), 2.44–2.52(m, 1H, 6 α-H), 3.71(d, J=7.1 Hz, 1H, 3-H), 3.72–3.85(br, 1H, OH), 4.12(d, J=8.6 Hz, 1H, 20 β-H), 4.24(d, J=8.6 Hz, 1H, 20 α-H), 4.42(dd, J=6.5, 10.5 Hz, 1H, 7-H), 4.86(d, J=8.2 Hz, 1H, 5-H), 5.21–5.30(m, 2H, Bn), 5.32(brs, 1H, 2'-H), 5.62(d, J=7.1 Hz, 1H, 2-H), 5.94(t, J=8.9 Hz, 1H, 13-H), 6.40(s, 1H, 10-H), 7.23–7.68(m, 13H, Ar), 8.06(d, J=7.7 Hz, 2H, Ar).

$^1$H-NMR (500 MHz, CDCl$_3$) of the oxime alcohol compound (compound (15-2)).

σ(ppm).

0.49–0.63(m, 6H, TES), 0.93(t, J=7.9Hz, 9H, TES), 1.15 (s, 3H, 17-CH$_3$), 1.20(s, 3H, 16-CH$_3$), 1.65(s, 3H, 19-CH$_3$), 1.68(s, 3H, 18-CH$_3$), 1.79–2.37(m, 3H), 1.86 (s, 3H, 4-Ac), 2.21 (s, 3H, 10-Ac), 2.45–2.58(m, 1H), 3.66(d, J=7.3 Hz, 1H, 3-H), 3.70–3.81(m, 1H), 4.074.32(m, 2H, 20-H), 4.33–4.48(m, 1H, 7-H), 4.79–4.94(m, 1H, 5-H), 5.18–5.32 (m, 3H, Bn, 2'-H), 5.59–5.71(m, 1H, 2-H), 5.90(t, J=9.2 Hz, 1H, 13-H), 6.36(s, 1H, 10-H), 7.22–7.71(m, 13H, Ar), 7.93–8.11(m, 2H, Ar).

Example 9

Production Method for Benzoylamino-alcohol Compound—(2)

Using the oxime alcohol compound obtained in Example 7 as a starting material, preparation of benzoylamino-alcohol compound according to Reaction Scheme 10 below was tried.

Reaction Scheme 10

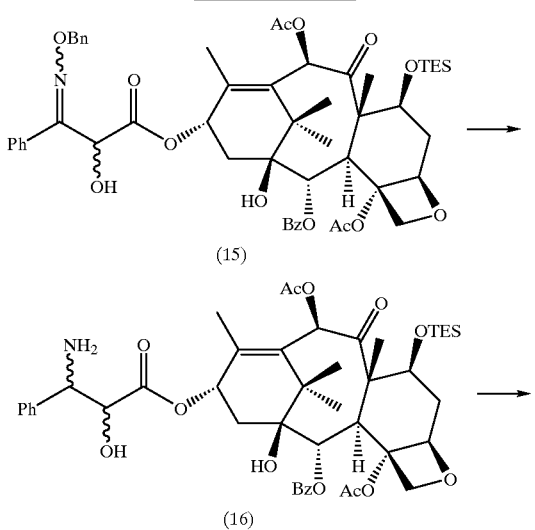

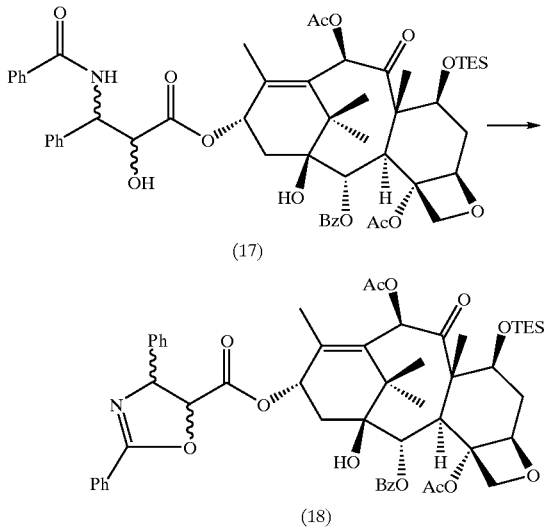

To 344 mg of oxime alcohol compound (15) obtained in Example 7 were added 5 ml of ethanol, 100 mg of 10% palladium-carbon, 681 mg of ammonium formate and the mixture was reacted at room temperature for 64 hours to obtain an amino-alcohol compound (compound (16), C$_{46}$H$_{61}$NO$_{13}$Si, molecular weight of 864.07).

To 156 mg of said compound (16) were added 2 ml of ethyl acetate, 2 ml of aqueous saturated sodium hydrogencarbonate, and 0.042 ml of benzoyl chloride and the mixture was reacted at room temperature for 3 hours to obtain a benzoylamino-alcohol compound (compound (17), C$_{53}$H$_{65}$NO$_{14}$Si, molecular weight of 968.18).

This compound was dissolved in chloroform-d and analyzed by $^1$H-NMR. Assignment of respective peaks was made to determine its chemical structure and thus it was confirmed to have a structure indicated as compound (17) in Reaction Scheme 10.

$^1$H-NMR (500 MHz, CDCl$_3$) of the benzoylamino-alcohol compound (compound (17)).

σ(ppm).

0.52–0.63(m, 6H, TES), 0.89–0.96(m, 9H, TES), 1.13(s), 1.14(s), 1.21(s), 1.22(s), 1.68(s), 1.72(s), 1.85–1.92(m, 1H), 2.11–2.35(m, 2H), 2.16(s), 2.17(s), 2.39(s), 2.44(s), 2.48–2.58(m, 1H), 3.30–3.40(m, 1H), 3.78–3.83(m, 1H), 4.12–4.20(m, 1H), 4.254.35(m, 1), 4.40–4.48(m 1H), 4.79–4.98(m, 2H), 5.63–5.70(m, 1H), 5.76–5.80(m, 1H), 6.00–6.10(m, 1H), 6.39(s), 6.40(s), 7.17–8.30(m, 15H, Ar).

Example 10

Production Method for Oxazoline Compound—(2)

Using the benzoylamino-alcohol compound obtained in Example 9 as a starting material, preparation of an oxazoline compound according to Reaction Scheme 10 above was tried.

To 117 mg of the benzoylamino-alcohol compound (17) obtained in Example 9 were added 2 ml of toluene, 31 mg of triphenylphosphine, and 0.054 ml of diethyl azodicarboxylate and the mixture was reacted at 0° C. for 1 hour to obtain an oxazoline compound (compound (18), C$_{53}$H$_{63}$NO$_{13}$Si, molecular weight of 950.17).

This compound was dissolved in chloroform-d and analyzed by $^1$H-NMR. Assignment of respective peaks was made to determine its chemical structure and thus it was confirmed to have a structure indicated as compound (18) in Reaction Scheme 10.

$^1$H-NMR (500 MHz, CDCl$_3$) of the oxazoline compound (compound (18)).

σ(ppm).

0.50–0.66(m 6H, TES), 0.80–0.99(m, 9H, TES), 1.20(s), 1.21(s), 1.23(s), 1.69(s), 1.72(s), 1.85–1.95(m), 1.96(s), 1.99 (s), 2.07(s), 2.16(s), 2.19(s), 2.20–2.60(m), 3.82–3.85(m), 4.10–4.35(m), 4.46–4.52(m), 4.87–4.97(m), 5.53–5.71(m), 6.15–6.49(m), 7.35–7.65(m), 8.08–8.25(m).

Example 11

Separation of Diastereomers—(2)

190 mg of the compound (18) obtained in Example 10 was subjected to separation of diastereomers using an ODS column according to Reaction Scheme 11. The separation conditions were as follows.

Column: Soken-pak φ100 mm×500 mm (Soken Kagaku)
Solvent: Methanol/water=90/10
Flow rate: 125 ml/minute
Detector: Ultraviolet detector (230 nm)

Reaction Scheme 11

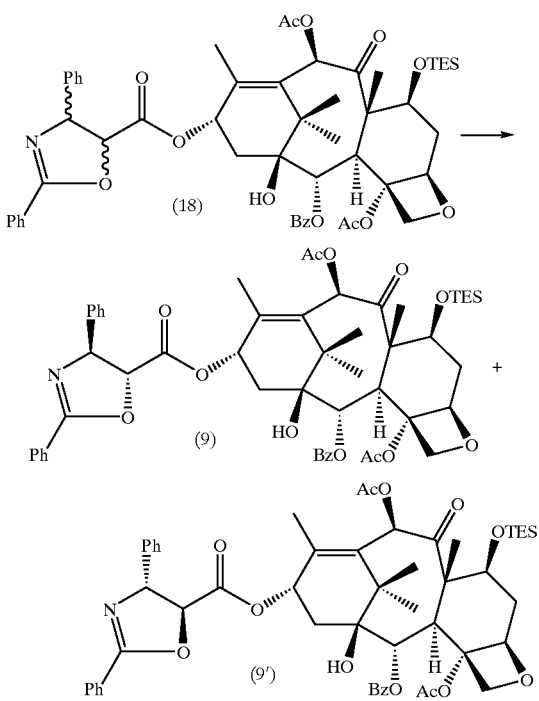

Under the above conditions, two fractions were obtained, which were each concentrated to obtain 91 mg of the compound (9) having a desired stereospecific configuration (4'S, 5'R) and 32 mg of the compound (9') having an undesired stereospecific configuration (4'R, 5'S). These respective compounds were dissolved in chloroform-d and analyzed by $^1$H-NMR. Assignment of respective peaks was made to determine their chemical structure. The results obtained are shown below.

$^1$H-NMR (500 MHz, CDCl$_3$) of the compound having a stereospecific configuration (4'S, 5'R) (compound (9)).

σ(ppm).

0.50–0.65(m, 6H, TES), 0.92(t, J-8.2 Hz, 9H, TES), 1.20(s,3H, 17-CH,), 1.23(s, 3H, 16-CH$_3$), 1.69(s,3H, 19-CH$_3$), 1.72(s, 1H, OH), 1.85–1.95(m, 1H, 6 β-H), 1.99(s, 3H, 18-CH$_3$), 2.07 (s, 3H, 4-Ac), 2.16 (s, 3H, 10-Ac), 2.27(dd, J=8.6, 15.3 Hz, 1H, 14-H), 2.38(dd, J=9.4, 15.3 Hz, 1H, 14-H), 2.55(ddd, J=6.7, 10.1, 14.6 Hz, 1H, 6 α-H), 3.84(d, J=7.2 Hz, 1H, 3-H), 4.14(d, J=8.5 Hz, 1H, 20 β-H), 4.29(d, J=8.5 Hz, 1H, 20 α-H), 4.50(dd, J=6.5, 10.5 Hz, 1H, 7-H), 4.95(d, J=6.6 Hz, 2H, 2'-H, 5-H), 5.60(d, J=6.6 Hz, 1H, 3'-H), 5.68(d, J=7.2 Hz, 1H, 2-H), 6.20(dd, J=8.6, 9.4 Hz, 1H, 13-H), 6.43(s, 1H, 10-H), 7.35–7.44(m, 5H, Ar), 7.46–7.54(m, 4H, Ar), 7.55–7.65(m, 2H, Ar), 8.08(d, J=7.1 Hz, 2H, Ar), 8.23(d, J=7.0 Hz, 2H, Ar).

$^1$H-NMR (500 MHz, CDCl$_3$) of the compound having a stereospecific configuration (4'R, 5'S) (compound (9')).

σ(ppm).

0.52–0.66(m, 6H, TES), 0.95(t, J=7.95 Hz, 9H, TES), 1.21(s,3H, 17-CH$_3$), 1.24(s, 3H, 16-CH$_3$), 1.69(s,3H, 19-CH$_3$), 1.70(s, 1H, OH), 1.89(ddd, J=2.1, 10.7, 14.3 Hz, 1H, 6 β-H), 1.96(s, 3H, 18-CH$_3$), 2.15 (s, 3H, 4-Ac), 2.19 (s, 3H, 10-Ac), 2.26(dd, J=8.4, 15.2 Hz, 1H, 14-H), 2.35(dd, J=9.2, 15.2 Hz, 1H, 14-H), 2.53(ddd, J=6.7, 9.6, 14.3 Hz, 1H, 6 α-H), 3.83(d, J=7.1 Hz, 1H, 3-H), 4.15(d, J=8.2 Hz, 1H, 20 β-H), 4.28(d, J=8.2 Hz, 1H, 20 α-H), 4.50(dd, J=6.7, 10.7Hz, 1H, 7-H), 4.89(dd, J=2.1, 9.6 Hz, 1H, 5-H), 4.96(d, J=6.4 Hz, 1H, 2'-H), 5.56(d, J=6.4Hz, 1H, 3'-H), 5.68(d, J=7.1 Hz, 1H, 2-H), 6.31(dd, J=8.4, 9.4 Hz, 1H, 13-H), 6.47(s, 1H, 10-H), 7.35–7.51(m, 9H, Ar), 7.55–7.64(m, 2H, Ar), 8.06(dd, J=1.4, 8.4 Hz, 2H, Ar), 8.09(dd, J=1.5, 8.5 Hz, 2H, Ar).

Example 12

Production Method for Paclitaxel—(2)

Using the compounds obtained in Example 11 as a starting material, preparation of paclitaxel according to Reaction Scheme 12 below was tried.

Reaction Scheme 12

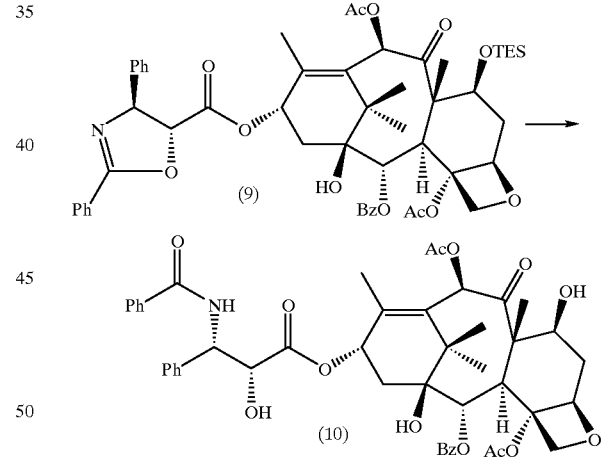

To 129 mg of the compound (9) obtained in Example 11 were added 6 ml of 0.1 N aqueous hydrochloric acid solution and 9 ml of methanol and the mixture was reacted at 60° C. for 1 hour and subsequently at 80° C. for 2 hours under reflux. After cooling the reaction mixture to room temperature, 3 ml of aqueous saturated sodium hydrogen-carbonate was added thereto and the mixture was reacted for 14.5 hours. After the treatment, the reaction mixture was purified through a silica gel column to obtain a compound (10).

The compound was dissolved in chloroform-d and analyzed by $^1$H-NMR. Assignment of respective peaks was made to determine its chemical structure and thus it was confirmed that the compound was paclitaxel.

Example 13
Production Method for Benzoylamino-alcohol Compound—(3)

In Example 9, 10% palladium-carbon was used as the palladium compound. However, similar compounds could be prepared using palladium black instead. Using the oxime alcohol compound having the desired stereospecific configuration obtained in Example 8 as a starting material, preparation of benzoylamino-alcohol compound according to Reaction Scheme 13 below was tried.

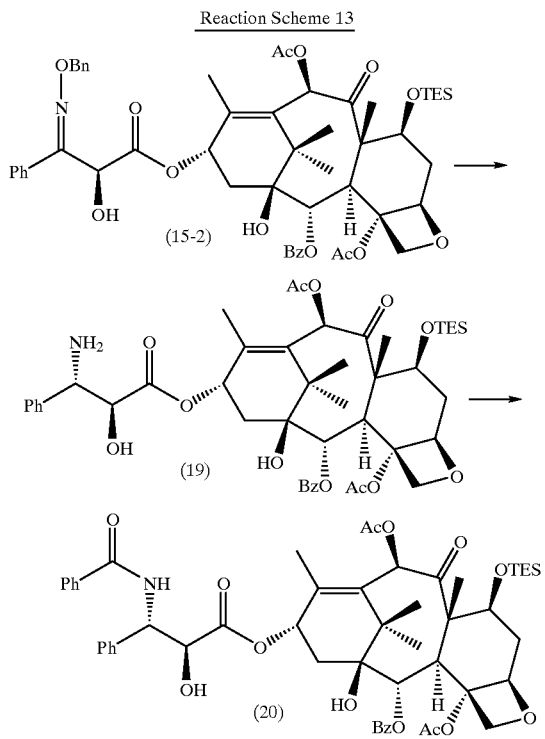

Reaction Scheme 13

To 46 mg of the oxime alcohol compound (15-2) obtained in Example 8 were added 3 ml of acetic acid, 100 mg of palladium black, and 47 mg of ammonium formate and the mixture was reacted at room temperature for 3 hours to obtain an amino-alcohol compound (compound (19), $C_{46}H_{61}NO_{13}Si$, molecular weight of 864.07).

To 157 mg of said compound (19) were added 2 ml of ethyl acetate, 2 ml of aqueous saturated sodium hydrogencarbonate, and 0.012 ml of benzoyl chloride and the mixture was reacted at room temperature for 3 hours to obtain a benzoylamino-alcohol compound (compound (20), $C_{53}H_{65}NO_{14}Si$, molecular weight of 968.18).

This compound was dissolved in chloroform-d and analyzed by $^1$H-NMR. Assignment of respective peaks was made to determine its chemical structure and thus it was confirmed to have a structure indicated as compound (20) in Reaction Scheme 13. This compound could be used to produce an oxazoline compound according to Example 10, from which paclitaxel could be produced as in Example 12.

$^1$H-NMR (500 MHz, $CDCl_3$) of the benzoylamino-alcohol compound (compound (20)).

σ(ppm).

0.52–0.65(m, 6H, TES), 0.93(t, J=7.9 Hz, 9H, TES), 1.11(s, 3H, 17-$CH_3$), 1.20(s, 3H, 16-$CH_3$), 1.66(s, 3H, 19-$CH_3$), 1.68(s, 3H, 18-$CH_3$), 1.85–1.92(m, 1H), 2.10–2.30 (m, 2H), 2.15(s, 3H, 4-Ac), 2.42(s, 3H, 10-Ac), 2.49–2.58 (m, 1H), 3.78(d, J=7.0 Hz, 1H, 3-H), 4.14(d, J=8.3 Hz, 1H, 20 β-H), 4.28(d, J=8.3 Hz, 1H, 20 α-H), 4.43(dd, J=6.7, 10.3 Hz, 1H, 7-H), 4.88(d, J=3.7 Hz, 1H, 2'-H), 5.22(d, J=8.8 Hz, 1H, 5-H), 5.65(d, J=7.0 Hz, 1H, 2-H), 5.80(dd, J=3.7, 8.6 Hz, 1H, 3'-H, 6.05(t, J=8.7 Hz, 1H, 13-H), 6.38(s, 1H, 10-H), 7.30–8.13(m, 16H, Ar, NH).

Example 14
Production Method for Oxime Alcohol Compound—(5)

Thus far the production methods for paclitaxel were described. However, its derivatives could be produced similarly. Hereafter, the production method for the compound represented by the general formula (I) in which $R^3$ is a p-methoxyphenyl group will be explained.

To obtain an oxime alcohol compound the reaction was carried out according to the following reaction scheme 14.

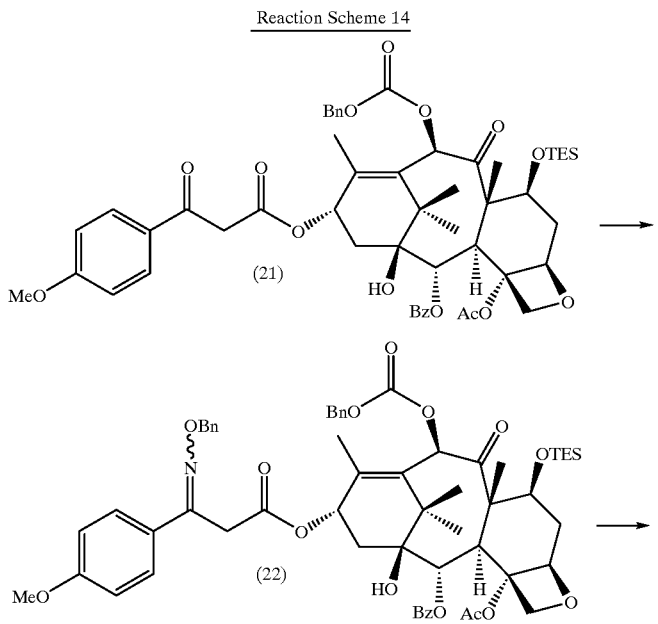

Reaction Scheme 14

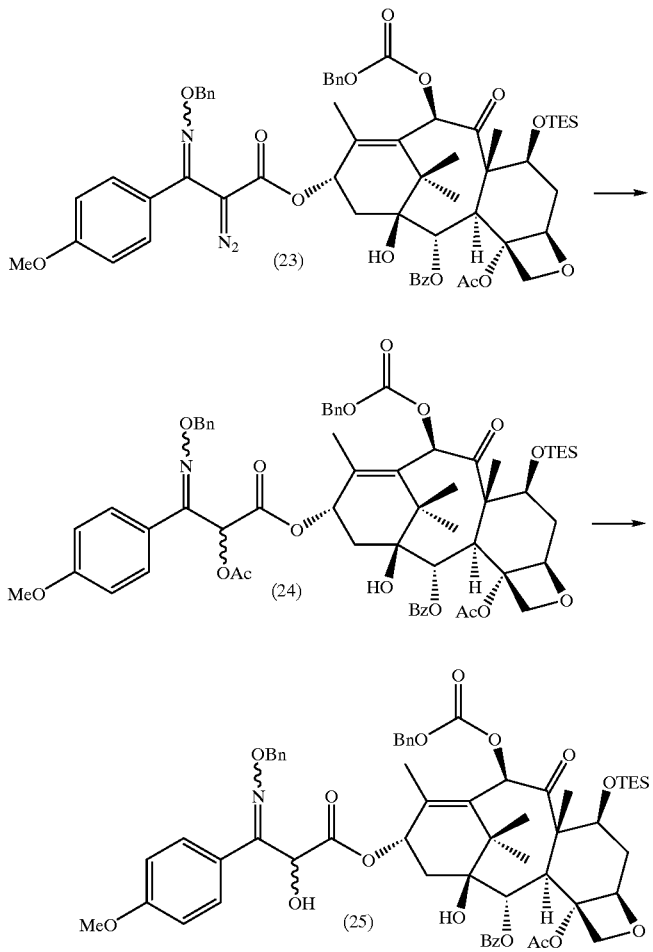

To 410 mg of an ester compound whose 3'-position is a p-methoxyphenyl group (7-triethylsilyl-10-benzyloxycarbonyl-10-deacetyl-13-(3-p-methoxyphenyl-3-keto-propanoyl)-baccatin III, compound (21), $C_{53}H_{64}O_{15}Si$, molecular weight: 969.17) were added 120 mg of 0-benzylhydroxylamine hydrochloride and 3 ml of pyridine and the mixture was reacted at room temperature for 15 hours to obtain an oxime compound (compound (22), $C_{60}H_{71}NO_{15}Si$, molecular weight of 1,074.30).

To the compound (22) were added 3 ml of acetonitrile, 128 mg of tosyl azide, 0.18 ml of triethylamine, and 0.022 ml of 1,8-diazabicyclo [5.4.0]-7-undecene and the mixture was reacted at room temperature for 14 hours to obtain a diazo-oxime compound (compound (23), $C_{60}H_{69}N_3O_{15}Si$, molecular weight of 1,100.30).

To 354 mg of the compound (23) were added 168 mg copper acetylacetonate, 3 ml of acetic acid and the mixture was reacted at 60° C. for 70 hours to obtain an acetoxyoxime compound (compound (24), $C_{62}H_{73}NO_{17}Si$, molecular weight of 1,132.34).

Then, to 316 mg of the compound (24) were added 5 mg of 1-chloro-3-hydroxytetrabutyldistanoxane and 3 ml of ethanol and the mixture was reacted at 70° C. for 40 hours to obtain an oxime alcohol compound (compound (25), $C_{60}H_{71}NO_{16}Si$, molecular weight of 1,090,30).

The compound was dissolved in chloroform-d and analyzed by $^1$H-NMR. Assignment of respective peaks was made to determine its chemical structure and thus it was confirmed to have a structure indicated as compound (25) in Reaction Scheme 14.

$^1$H-NMR (500 MHz, $CDCl_3$) of the oxime alcohol compound (compound (25)).

σ(ppm).

0.51–0.65(m, 6H), 0.75–0.99(m, 9H), 1.14(s, 3H), 1.81(s, 3H), 1.84–1.95(m, 1H), 2.12–2.39(m, 2H), 2.20(s, 3H), 2.47–2.58(m, 1H), 3.53–3.68(m, 1H), 3.74(d, J=7.0 Hz, 1H), 3.83(s, 3H), 4.14(d, J=8.4 Hz, 1H), 4.27(d, J=8.4 Hz, 1H), 4.44(dd, J=6.7, 10.4 Hz, 1H), 4.91(d, J=8.6 Hz, 1H), 5.09–5.30(m, 5H), 5.65(d, J=7.0 Hz, 1H,), 6.09(t, J=8.7 Hz, 1H), 6.22(s, 1H), 6.93(d, J=8.8 Hz, 2H), 7.12–7.51(m, 7H), 7.56–7.63(m, 1H), 7.70(d, J=9.2 Hz, 2H), 8.05(d, J=7.3 Hz, 2H).

Example 15

Production Method for Benzoylamino-alcohol Compound—(4)

Using the oxime alcohol compound obtained in Example 14 as a starting material, preparation of benzoylamino-alcohol compound according to Reaction Scheme 15 below was tried.

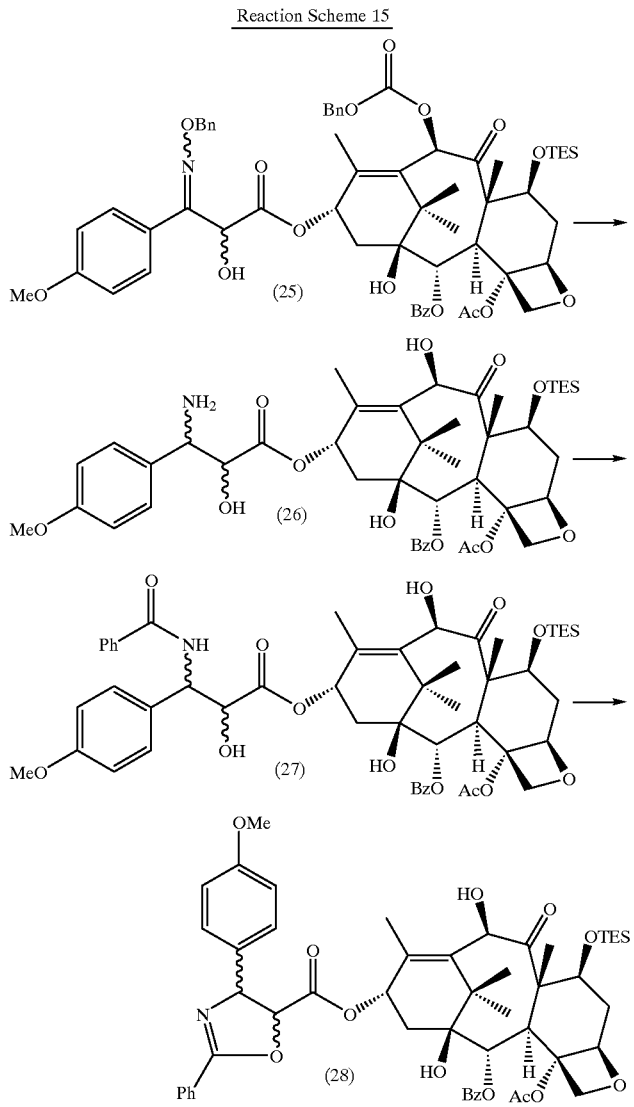

Reaction Scheme 15

To 137 mg of oxime alcohol compound (25) obtained in Example 14 were added 5 ml of methanol, 200 mg of 10% palladium-carbon, 340 mg of ammonium formate and the mixture was reacted at room temperature for 17 hours to obtain an amino-alcohol compound (compound (26), $C_{45}H_{61}NO_{13}Si$, molecular weight of 852.06).

To 156 mg of said compound (26) were added 3 ml of ethyl acetate, 3 ml of aqueous saturated sodium hydrogencarbonate, and 0.035 ml of benzoyl chloride and the mixture was reacted at room temperature for 3 hours to obtain a benzoylamino-alcohol compound (compound (27), $C_{52}H_{65}NO_{14}Si$, molecular weight of 956.17).

This compound was dissolved in chloroform-d and analyzed by $^1$H-NMR. Assignment of respective peaks was made to determine its chemical structure and thus it was confirmed to have a structure indicated as compound (27) in Reaction Scheme 15.

$^1$H-NMR (500 MHz, CDCl$_3$) of the benzoylamino-alcohol compound (compound (27)).

σ(ppm).

0.47–0.63(m, 6H), 0.86–1.02(m, 9H), 1.07(s, 3H), 1.13(s, 3H), 1.64(s, 3H), 1.72(s, 3H), 1.86–1.95(m, 1H), 2.09–2.39 (m, 2H), 2.35(s, 3H), 2.44–2.52(m, 1H), 3.75(s, 3H), 3.84(d, J=7.0 Hz, 1H), 4.15(d, J=8.2 Hz, 1H), 4.28(d, J=8.2 Hz, 1H), 4.36(dd, J=6.7, 10.3 Hz, 1H), 4.84(s, 1H), 4.93(d, J=8.2 Hz, 1H), 5.07(s, 1H), 5.62(d, J=7.0 Hz, 1H), 5.72(dd, J=3.8, 8.4 Hz, 1H), 6.02(t, J=8.5 Hz, 1H), 6.86(d, J=8.2 Hz, 2H), 7.12–7.84(m, 10H), 8.04(d, J=8.3 Hz, 2H).

Example 16

Production Method for Oxazoline Compound—(3)

Using the benzoylamino-alcohol compound obtained in Example 15 as a starting material, preparation of an oxazoline compound according to Reaction Scheme 15 above was tried.

To 135 mg of the benzoylamino-alcohol compound (27) obtained in Example 15 were added 3 ml of dichloromethane, 68 mg of triphenylphosphine, and 0.041 ml of diethyl azodicarboxylate and the mixture was reacted at room temperature for 13 hours to obtain an oxazoline compound (compound (28), $C_{52}H_{63}NO_{13}Si$, molecular weight of 938.15).

This compound was dissolved in chloroform-d and analyzed by $^1$H-NMR. Assignment of respective peaks was made to determine its chemical structure and thus it was confirmed to have a structure indicated as compound (28) in Reaction Scheme 15.

$^1$H-NMR (500 MHz, CDCl$_3$) of the oxazoline compound (compound (28)).

σ(ppm).

0.46–0.63(m, 6H), 0.88–1.00(m, 9H), 1.08(s, 3H), 1.16(s, 3H), 1.63(s, 3H), 1.73(s, 3), 1.77–2.54(m, 3H), 3.76(s, 3H), 4.09–4.45(m, 3H), 4.91–4.96(m, 1H), 5.06(s, 3H), 5.59–5.68(m, 2H), 5.85(dd, J=4.9, 7.6 Hz, 1H), 6.11(t, J=8.4 Hz, 1H), 6.85–8.24(m, 14H).

Example 17

Production Method for 3'-p-Methoxyphenyl-3'-Dephenylpaclitaxel

Using the compound obtained in Example 16 as a starting material, preparation of 3'-p-methoxyphenyl-3'-dephenylpaclitaxel according to Reaction Scheme 16 below was tried.

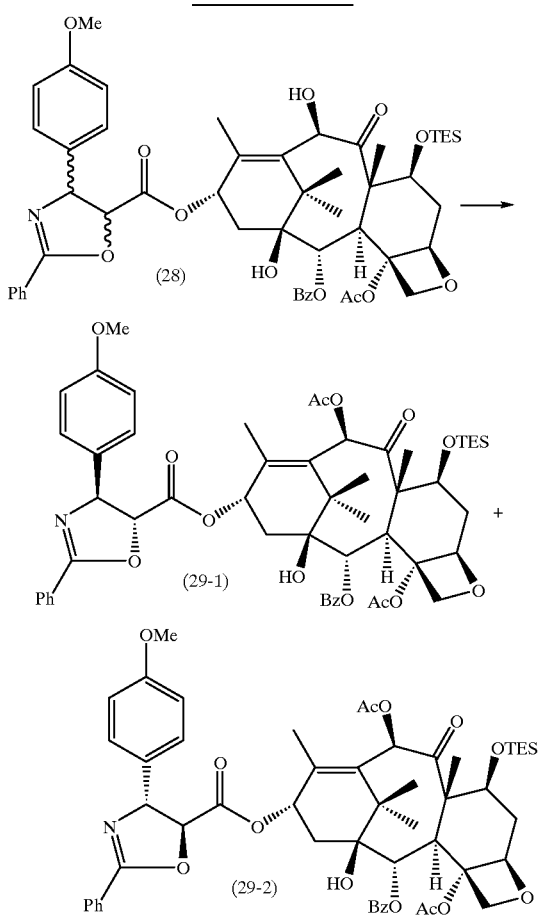

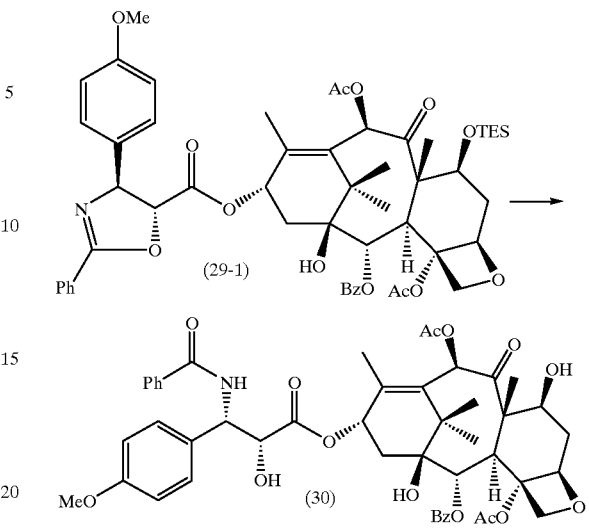

To 212 mg of the oxazoline compound obtained in Example 16 (compound (28)) were added 0.10 ml of acetyl chloride, 244 mg of 4-dimethylaminopyridine, and 5 ml of dichloromethane and the mixture was reacted at 0° C. to room temperature for 3.5 hours to obtain oxazoline compounds whose 10-positions were acetylated (compounds (29-1) and (29-2), C$_{54}$H$_{65}$NO$_{14}$Si, molecular weight of 980.19). The isomer mixture was applied to a silica gel flush column to isolate a compound of which oxazoline ring has a stereospecific configuration (4'S, 5'R) (compound (29-1)).

To 103 mg of said compound (29-1) were added 6 ml of 0.1 N aqueous hydrochloric acid solution and 9 ml of methanol and the mixture was reacted at 60° C. for 1 hour and subsequently at 85° C. for 1.5 hours under reflux. After cooling the reaction mixture to room temperature, 3 ml of aqueous saturated sodium hydrogencarbonate was added thereto and the mixture was reacted for 16 hours. After the treatment, the reaction mixture was purified through a silica gel column to obtain a paclitaxel derivative (compound (30), C$_{48}$H$_{53}$NO$_{15}$, molecular weight of 883.94).

This compound was dissolved in chloroform-d and analyzed by $^1$H-NMR. Assignment of respective peaks was made to determine its chemical structure and thus it was confirmed to have a structure indicated as compound (30) in Reaction Scheme 16.

$^1$H-NMR (500 MHz, CDCl$_3$) of 3'-p-methoxyphenyl-3'-dephenylpaclitaxel (compound (30)).

σ(ppm).

1.15(s, 3H), 1.24(s, 3H), 1.69(s, 3H), 1.81(s, 3H), 1.85–1.92(m, 1H), 2.24(s, 3H), 2,27–2.37(m, 2H), 2.38(s, 3H), 2,50–2.59(m, 1H), 3.80(s, 3H), 3.81(d, J=7.0 Hz, 1H), 4.20(d, J=8.5 Hz, 1H), 4.31(d, J=8.5 Hz, 1H), 4.38–4.43(m, 1H), 4.75(d, J=2.8 Hz, 1H), 4.95(dd, J=1.5, 9.2 Hz, 1H), 5.68(d, J=7.0 Hz, 1H), 5.72(dd, J=2.8, 8.9 Hz, 1H), 6.22(t, J=9.0 Hz, 1H), 6.28(s, 1H), 6.9(d, J=8.9 Hz, 1H), 6.94(d, J=8.5 Hz, 2H), 7.34–7.57(m, 7H), 7.61(t, J=7.3 Hz, 1H), 7.73(d, J=7.3 Hz, 2H), 8.13(d, J=7.4 Hz, 2H).

What is claimed is:

1. A taxoid derivative represented by general formula (I);

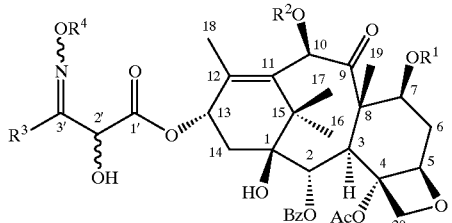

(I)

(where $R^1$ and $R^2$ simultaneously or independently represent a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^4$ represents any one of a benzyl group, a methyl group, or an ethyl group, Bz represents a benzoyl group, and Ac represents an acetyl group).

2. A method for producing a taxoid derivative, characterized in that the taxoid derivative as claimed in claim 1, represented by general formula (I) is obtained using as a starting material a baccatin compound represent by general formula (a);

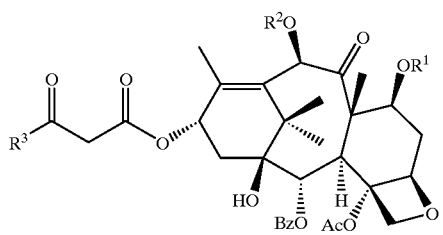

(a)

(where $R^1$ and $R^2$ simultaneously or independently represent a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, Bz represents a benzoyl group, and Ac represents an acetyl group), through intermediate compounds represented by general formulae (b), (c), and (d);

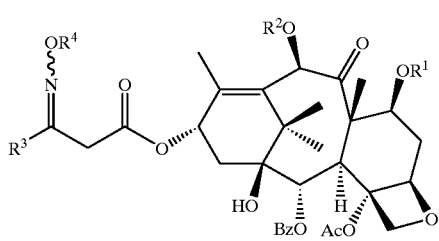

(b)

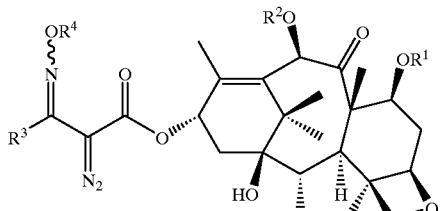

(c)

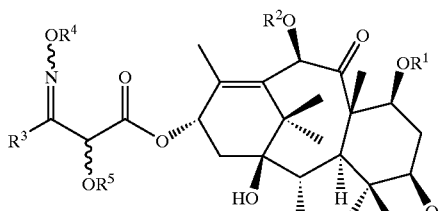

(d)

(in the above-mentioned formulae (b), (c), and (d), $R^1$ and $R^2$ simultaneously or independently represent a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^4$ represents any one of a benzyl group, a methyl group, or an ethyl group, $R^5$ represents an acyl group, Bz represents a benzoyl group, and Ac represents an acetyl group).

3. A method for producing a taxoid compound, characterized in that the taxoid compound such as paclitaxel represented by general formula (V);

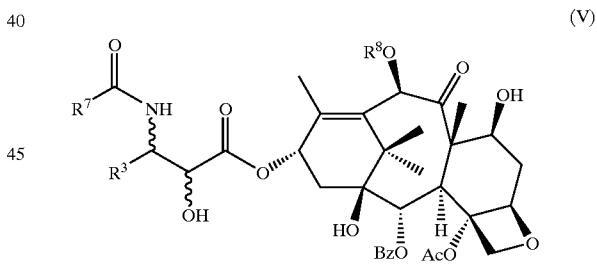

(V)

is obtained using as a starting material the taxoid derivative as claimed in claim 1, through intermediate compounds represented by general formulae (II), (III), and (IV);

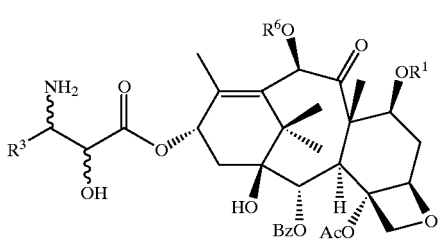

(II)

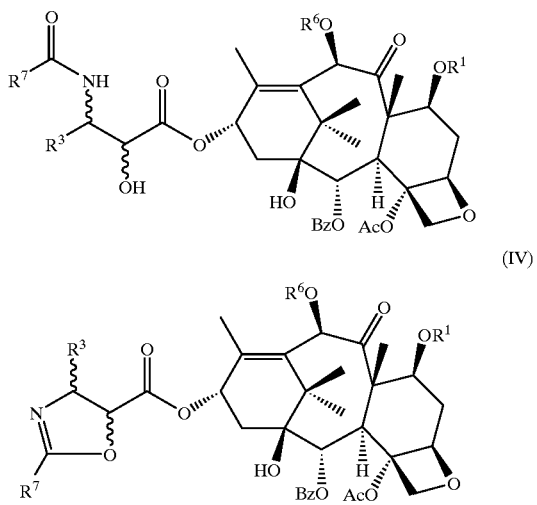

(in the above-mentioned formulae (II), (III), (IV), and (V), $R^1$ represents a protective group for a hydroxyl group, $R^3$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^6$ represents a hydrogen atom or a protective group for a hydroxyl group, $R^7$ represents any one of an unsubstituted or substituted phenyl group, an unsubstituted or substituted furyl group, an unsubstituted or substituted pyridinyl group, an alkyl group, a hydroxyalkyl group, a halogenated alkyl group, a cyclic alkyl group, or a thienyl group, $R^8$ represents a hydrogen atom or an acyl group, Bz represents a benzoyl group, and Ac represents an acetyl group).

* * * * *